United States Patent
Knox et al.

(10) Patent No.: US 11,129,724 B2
(45) Date of Patent: Sep. 28, 2021

(54) STEMLESS PROSTHESIS ANCHOR COMPONENT

(71) Applicant: HOWMEDICA OSTEONICS CORP., Mahwah, NJ (US)

(72) Inventors: Kevin P. Knox, Fort Wayne, IN (US); Brian M. Strzelecki, Fort Wayne, IN (US); Shawn M. Gargac, Fort Wayne, IN (US); Brian C. Hodorek, Winona Lake, IN (US); Pierric Deransart, Saint Martin d'uriage (FR); Jean-Emmanuel Cardon, Domene (FR); Austin Wyatt Mutchler, Warsaw, IN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 3 days.

(21) Appl. No.: 16/320,860

(22) PCT Filed: Jun. 22, 2017

(86) PCT No.: PCT/US2017/038843
§ 371 (c)(1),
(2) Date: Jan. 25, 2019

(87) PCT Pub. No.: WO2018/022227
PCT Pub. Date: Feb. 1, 2018

(65) Prior Publication Data
US 2019/0159906 A1    May 30, 2019

Related U.S. Application Data

(60) Provisional application No. 62/368,036, filed on Jul. 28, 2016.

(51) Int. Cl.
*A61F 2/40* (2006.01)
*A61F 2/46* (2006.01)
(Continued)

(52) U.S. Cl.
CPC .............. *A61F 2/4014* (2013.01); *A61F 2/40* (2013.01); *A61F 2/4003* (2013.01);
(Continued)

(58) Field of Classification Search
CPC ..... A61F 2002/30858; A61F 2/40–2002/4051; A61F 2/4081–2002/4096
See application file for complete search history.

(56) References Cited

U.S. PATENT DOCUMENTS

| 448,126 A | 3/1891 | Craig |
| 1,065,456 A | 6/1913 | Lowrey |

(Continued)

FOREIGN PATENT DOCUMENTS

| DE | 4220217 | 12/1993 |
| DE | 10233204 | 1/2004 |

(Continued)

OTHER PUBLICATIONS

Barth, et al., "Is global humeral head offset related to intramedullary canal width? A computer tomography morphometric study," Journal of Experimental Orthopaedics, 2018, vol. 5, pp. 1-8.
(Continued)

*Primary Examiner* — Rebecca S Preston
(74) *Attorney, Agent, or Firm* — Duane Morris LLP

(57) ABSTRACT

A prosthesis assembly is provided that includes a base member (104) that has a helical structure (224) and one or more pathways. The helical structure extends between a first end and a second end. The pathway is accessible from the second end and is directed toward the first end through the helical structure. The pathway is located inward of an outer periphery of the helical structure, e.g., adjacent to an inner periphery of the helical structure. The pathway extends in a space between successive portions of the helical structure. The prosthesis assembly includes a locking device (108) that
(Continued)

has a support member and an arm (110) I/O that projects away from the support member. The arm is configured to be disposed in the pathway when the support member is disposed adjacent to the second end of the base member. The arm is disposed through bone in the space between successive portions of the helical structure when the prosthesis assembly is implanted.

16 Claims, 29 Drawing Sheets

(51) Int. Cl.
 *A61F 2/30* (2006.01)
 *A61B 17/16* (2006.01)
 *A61B 17/15* (2006.01)
 *A61F 2/00* (2006.01)

(52) U.S. Cl.
 CPC .......... *A61F 2/4059* (2013.01); *A61F 2/4637* (2013.01); *A61B 17/15* (2013.01); *A61B 17/1684* (2013.01); *A61F 2/0077* (2013.01); *A61F 2/30767* (2013.01); *A61F 2002/30011* (2013.01); *A61F 2002/3079* (2013.01); *A61F 2002/30289* (2013.01); *A61F 2002/30408* (2013.01); *A61F 2002/30593* (2013.01); *A61F 2002/30784* (2013.01); *A61F 2002/30858* (2013.01); *A61F 2002/30873* (2013.01); *A61F 2002/30884* (2013.01); *A61F 2002/4007* (2013.01); *A61F 2002/4062* (2013.01); *A61F 2002/4074* (2013.01)

(56) References Cited

U.S. PATENT DOCUMENTS

| | | |
|---|---|---|
| 1,123,730 A | 1/1915 | Greenfield |
| 2,444,099 A | 6/1948 | Hennessey, Jr. |
| 2,886,081 A | 5/1959 | Cowley |
| 3,523,395 A | 8/1970 | Rutter et al. |
| 3,559,514 A | 2/1971 | Brownfield |
| 3,609,056 A | 9/1971 | Hougen |
| 3,738,217 A | 6/1973 | Walker |
| 4,042,980 A | 8/1977 | Swanson et al. |
| 4,147,464 A | 4/1979 | Watson et al. |
| 4,250,600 A | 2/1981 | Gunther |
| 4,261,062 A | 4/1981 | Amstutz et al. |
| 4,406,023 A | 9/1983 | Harris |
| 4,550,450 A | 11/1985 | Kinnett |
| 4,623,353 A | 11/1986 | Buechel et al. |
| 4,632,111 A | 12/1986 | Roche |
| 4,662,891 A * | 5/1987 | Noiles .................. A61F 2/34 623/22.31 |
| 4,743,262 A | 5/1988 | Tronzo |
| 4,865,605 A | 9/1989 | Dines et al. |
| 4,883,491 A | 11/1989 | Mallory et al. |
| 4,964,865 A | 10/1990 | Burkhead et al. |
| 4,986,833 A | 1/1991 | Worland |
| 5,026,373 A | 6/1991 | Ray et al. |
| 5,032,132 A | 7/1991 | Matsen et al. |
| 5,044,393 A | 9/1991 | Jiles |
| 5,080,673 A | 1/1992 | Burkhead et al. |
| 5,112,338 A | 5/1992 | Anspach, III |
| 5,163,964 A | 11/1992 | Lazzeri et al. |
| 5,171,277 A | 12/1992 | Roger |
| 5,203,653 A | 4/1993 | Kudla |
| 5,257,995 A | 11/1993 | Umber et al. |
| 5,282,865 A | 2/1994 | Dong |
| 5,358,526 A | 10/1994 | Tornier |
| 5,489,309 A | 2/1996 | Lackey et al. |
| 5,489,310 A | 2/1996 | Mikhail |
| 5,507,817 A | 4/1996 | Craig et al. |
| 5,540,697 A | 7/1996 | Rehmann et al. |
| 5,591,170 A | 1/1997 | Spievack et al. |
| 5,658,290 A | 8/1997 | Lechot |
| 5,681,134 A | 10/1997 | Ebert |
| 5,702,486 A | 12/1997 | Craig et al. |
| 5,723,018 A | 3/1998 | Cyprien et al. |
| 5,776,194 A | 7/1998 | Mikol et al. |
| 5,800,551 A | 9/1998 | Williamson et al. |
| 5,810,524 A | 9/1998 | Wirth, Jr. et al. |
| 5,820,315 A | 10/1998 | Collard |
| 5,830,215 A | 11/1998 | Incavo et al. |
| 5,904,688 A | 5/1999 | Gilbert et al. |
| 5,919,195 A | 7/1999 | Wilson et al. |
| 5,954,727 A | 9/1999 | Collazo |
| 5,976,148 A | 11/1999 | Charpenet et al. |
| 6,045,582 A | 4/2000 | Prybyla |
| 6,063,124 A | 5/2000 | Amstutz |
| 6,099,214 A | 8/2000 | Lee et al. |
| 6,132,469 A | 10/2000 | Schroeder |
| 6,139,551 A | 10/2000 | Michelson et al. |
| 6,146,423 A | 11/2000 | Cohen et al. |
| 6,174,335 B1 | 1/2001 | Varieur et al. |
| 6,187,012 B1 | 2/2001 | Masini |
| 6,197,063 B1 | 3/2001 | Dews |
| 6,264,299 B1 | 7/2001 | Noda |
| 6,264,657 B1 | 7/2001 | Urbahns et al. |
| 6,306,171 B1 | 10/2001 | Conzemius |
| 6,364,910 B1 | 4/2002 | Shultz et al. |
| 6,368,271 B1 | 4/2002 | Sharratt |
| 6,368,353 B1 | 4/2002 | Arcand |
| 6,379,917 B1 | 4/2002 | Okun et al. |
| 6,409,730 B1 | 6/2002 | Green et al. |
| 6,508,840 B1 | 1/2003 | Rockwood, Jr. et al. |
| 6,520,994 B2 | 2/2003 | Nogarin |
| 6,537,278 B1 | 3/2003 | Johnson |
| 6,666,874 B2 | 12/2003 | Heitzmann et al. |
| 6,699,289 B2 | 3/2004 | Iannotti et al. |
| 6,736,851 B2 | 5/2004 | Maroney et al. |
| 6,746,452 B2 | 6/2004 | Tuke et al. |
| 6,783,549 B1 | 8/2004 | Stone et al. |
| 6,786,684 B1 | 9/2004 | Ecker |
| 6,797,006 B2 | 9/2004 | Hodorek et al. |
| 6,949,101 B2 | 9/2005 | McCleary et al. |
| 7,044,973 B2 | 5/2006 | Rockwood, Jr. et al. |
| 7,097,663 B1 | 8/2006 | Nicol et al. |
| 7,140,087 B1 | 11/2006 | Giltner |
| 7,160,328 B2 | 1/2007 | Rockwood, Jr. et al. |
| 7,169,184 B2 | 1/2007 | Dalla Pria |
| 7,175,663 B1 | 2/2007 | Stone |
| 7,179,084 B1 | 2/2007 | Kometas |
| 7,189,036 B1 | 3/2007 | Watson |
| 7,189,261 B2 | 3/2007 | Dews et al. |
| 7,204,854 B2 | 4/2007 | Guederian et al. |
| 7,217,271 B2 | 5/2007 | Wolford et al. |
| 7,344,565 B2 | 3/2008 | Seyer et al. |
| 7,465,319 B2 | 12/2008 | Tornier |
| 7,473,254 B2 | 1/2009 | White et al. |
| 7,476,228 B2 | 1/2009 | Abou |
| 7,476,253 B1 | 1/2009 | Craig et al. |
| 7,503,921 B2 | 3/2009 | Berthusen et al. |
| 7,572,259 B2 | 8/2009 | Desarzens et al. |
| 7,585,327 B2 | 9/2009 | Winslow |
| 7,615,080 B2 | 11/2009 | Ondrla |
| 7,637,703 B2 | 12/2009 | Khangar et al. |
| 7,637,909 B2 | 12/2009 | Lechot et al. |
| 7,648,530 B2 | 1/2010 | Habermeyer et al. |
| 7,670,382 B2 | 3/2010 | Parrott et al. |
| 7,678,150 B2 | 3/2010 | Tornier et al. |
| 7,744,602 B2 | 6/2010 | Teeny et al. |
| 7,749,227 B2 | 7/2010 | Lechot et al. |
| 7,758,650 B2 | 7/2010 | Dews et al. |
| 7,780,669 B2 | 8/2010 | Lechot et al. |
| 7,785,329 B2 | 8/2010 | Lechot et al. |
| 7,803,160 B2 | 9/2010 | Keller |
| 7,819,875 B2 | 10/2010 | Chana |
| 7,887,544 B2 | 2/2011 | Tornier et al. |
| 7,892,287 B2 | 2/2011 | Deffenbaugh |
| 7,922,769 B2 | 4/2011 | Deffenbaugh et al. |
| 7,927,335 B2 | 4/2011 | Deffenbaugh et al. |
| 7,927,376 B2 | 4/2011 | Leisinger et al. |

(56) References Cited

U.S. PATENT DOCUMENTS

| | | |
|---|---|---|
| D643,926 S | 8/2011 | Collins |
| 8,021,370 B2 | 9/2011 | Fenton et al. |
| 8,052,690 B2 | 11/2011 | Berthusen et al. |
| 8,114,089 B2 | 2/2012 | Divoux et al. |
| 8,162,947 B2 | 4/2012 | Dreyfuss |
| 8,182,541 B2 | 5/2012 | Long et al. |
| 8,187,282 B2 | 5/2012 | Tornier et al. |
| 8,192,497 B2 | 6/2012 | Ondrla |
| 8,202,275 B2 | 6/2012 | Wozencroft |
| 8,221,037 B2 | 7/2012 | Neitzell |
| 8,231,682 B2 | 7/2012 | LaFosse |
| 8,246,687 B2 | 8/2012 | Katrana et al. |
| 8,277,512 B2 | 10/2012 | Parrott et al. |
| 8,282,639 B2 | 10/2012 | Chana |
| 8,317,871 B2 | 11/2012 | Stone et al. |
| 8,409,798 B2 | 4/2013 | Luy et al. |
| 8,419,798 B2 | 4/2013 | Ondrla et al. |
| D685,474 S | 7/2013 | Courtney |
| 8,475,460 B1 | 7/2013 | Roger et al. |
| 8,480,674 B1 | 7/2013 | Roger et al. |
| 8,486,076 B2 | 7/2013 | Chavarria |
| 8,500,744 B2 | 8/2013 | Wozencroft et al. |
| 8,506,638 B2 | 8/2013 | Vanasse et al. |
| 8,512,410 B2 | 8/2013 | Metcalfe et al. |
| 8,545,506 B2 | 10/2013 | Long et al. |
| 8,591,592 B2 | 11/2013 | Dreyfuss |
| 8,641,773 B2 | 2/2014 | Bergin et al. |
| 8,647,387 B2 | 2/2014 | Winslow |
| 8,657,833 B2 | 2/2014 | Burgi et al. |
| 8,657,834 B2 | 2/2014 | Burgi et al. |
| 8,663,334 B2 | 3/2014 | Viscardi et al. |
| 8,690,958 B2 | 4/2014 | Klawitter et al. |
| 8,702,800 B2 | 4/2014 | Linares et al. |
| 8,721,727 B2 | 5/2014 | Ratron et al. |
| 8,740,907 B2 | 6/2014 | Penenberg |
| 8,753,402 B2 | 6/2014 | Winslow et al. |
| 8,771,275 B2 | 7/2014 | Xie et al. |
| 8,795,379 B2 | 8/2014 | Smith et al. |
| 8,834,471 B2 | 9/2014 | Roger et al. |
| 8,840,671 B2 | 9/2014 | Ambacher |
| 8,845,742 B2 | 9/2014 | Kusogullari et al. |
| 8,864,834 B2 | 10/2014 | Boileau et al. |
| 8,870,962 B2 | 10/2014 | Roche et al. |
| 8,876,908 B2 | 11/2014 | Katrana et al. |
| 8,882,845 B2 | 11/2014 | Wirth et al. |
| 8,992,623 B2 | 3/2015 | Hopkins et al. |
| 9,066,730 B2 | 6/2015 | McMinn et al. |
| 9,066,731 B2 | 6/2015 | Moore |
| 9,078,672 B1 | 7/2015 | Rossé |
| D745,678 S | 12/2015 | Courtney et al. |
| 9,233,003 B2 | 1/2016 | Roche et al. |
| 9,289,218 B2 | 3/2016 | Courtney, Jr. et al. |
| 9,326,865 B2 | 5/2016 | Katrana et al. |
| 9,364,334 B2 | 6/2016 | Katrana et al. |
| 9,498,345 B2 | 11/2016 | Burkhead, Jr. et al. |
| 9,510,839 B2 | 12/2016 | Maroney et al. |
| 9,603,712 B2 | 3/2017 | Bachmaier |
| 9,615,928 B2 | 4/2017 | Visser et al. |
| 9,820,859 B2 | 11/2017 | Gervasi et al. |
| 10,166,032 B2 | 1/2019 | Stone et al. |
| D840,539 S | 2/2019 | Courtney et al. |
| 10,335,285 B2 | 7/2019 | Viscardi et al. |
| 10,368,999 B2 | 8/2019 | Greiwe |
| 10,433,969 B2 | 10/2019 | Humphrey |
| 10,456,264 B2 | 10/2019 | Hodorek et al. |
| 10,463,499 B2 | 11/2019 | Emerick et al. |
| 2001/0034553 A1 | 10/2001 | Michelson |
| 2001/0047210 A1 | 11/2001 | Wolf |
| 2002/0116007 A1 | 8/2002 | Lewis |
| 2002/0156534 A1 | 10/2002 | Grusin et al. |
| 2003/0004573 A1 | 1/2003 | Bagby |
| 2003/0028253 A1 | 2/2003 | Stone et al. |
| 2003/0031521 A1 | 2/2003 | Haughton et al. |
| 2003/0125810 A1 | 7/2003 | Sullivan et al. |
| 2003/0163135 A1 | 8/2003 | Hathaway |
| 2003/0220646 A1 | 11/2003 | Thelen et al. |
| 2004/0049270 A1 | 3/2004 | Gewirtz |
| 2004/0097947 A1 | 5/2004 | Wolford et al. |
| 2004/0186586 A1 | 9/2004 | Seyer et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0220674 A1 | 11/2004 | Pria |
| 2004/0236339 A1 | 11/2004 | Pepper |
| 2004/0243136 A1 | 12/2004 | Gupta et al. |
| 2005/0107882 A1 | 5/2005 | Stone et al. |
| 2005/0112397 A1 | 5/2005 | Rolfe et al. |
| 2005/0159751 A1 | 7/2005 | Berthusen et al. |
| 2005/0209597 A1 | 9/2005 | Long et al. |
| 2005/0261775 A1 | 11/2005 | Baum et al. |
| 2005/0267478 A1 | 12/2005 | Corradi et al. |
| 2006/0004378 A1 | 1/2006 | Raines |
| 2006/0009852 A1 | 1/2006 | Winslow et al. |
| 2006/0015110 A1 | 1/2006 | Pepper |
| 2006/0058809 A1 | 3/2006 | Zink et al. |
| 2006/0089656 A1 | 4/2006 | Allard et al. |
| 2006/0195105 A1 | 8/2006 | Teeny et al. |
| 2006/0200165 A1 | 9/2006 | Tulkis |
| 2006/0200249 A1 | 9/2006 | Beguin et al. |
| 2007/0010825 A1 | 1/2007 | Leisinger et al. |
| 2007/0038303 A1 | 2/2007 | Myerson et al. |
| 2007/0093840 A1 | 4/2007 | Pacelli et al. |
| 2007/0100458 A1 | 5/2007 | Dalla Pria |
| 2007/0123890 A1 | 5/2007 | Way et al. |
| 2007/0123893 A1 | 5/2007 | O'Donoghue |
| 2007/0123909 A1 | 5/2007 | Rupp et al. |
| 2007/0156246 A1 | 7/2007 | Meswania et al. |
| 2007/0162141 A1 | 7/2007 | Dews et al. |
| 2007/0173945 A1 | 7/2007 | Wiley et al. |
| 2007/0212179 A1 | 9/2007 | Khangar et al. |
| 2007/0219562 A1 | 9/2007 | Slone et al. |
| 2007/0233132 A1 | 10/2007 | Valla |
| 2008/0021564 A1 | 1/2008 | Gunther |
| 2008/0077146 A1 | 3/2008 | Pernsteiner et al. |
| 2008/0195111 A1 | 8/2008 | Anderson |
| 2008/0249577 A1 | 10/2008 | Dreyfuss |
| 2009/0171462 A1 | 7/2009 | Poncet et al. |
| 2009/0270863 A1 | 10/2009 | Maisonneuve |
| 2009/0281630 A1 | 11/2009 | Delince et al. |
| 2009/0306782 A1 | 12/2009 | Schwyzer |
| 2010/0042214 A1 | 2/2010 | Nebosky et al. |
| 2010/0087927 A1 | 4/2010 | Roche et al. |
| 2010/0114326 A1 | 5/2010 | Winslow et al. |
| 2010/0191340 A1 | 7/2010 | Dreyfuss |
| 2010/0228352 A1 | 9/2010 | Courtney, Jr. et al. |
| 2010/0274360 A1 | 10/2010 | Gunther |
| 2010/0278601 A1 | 11/2010 | Beynon |
| 2011/0004215 A1 | 1/2011 | Bradley et al. |
| 2011/0028977 A1 | 2/2011 | Rauscher et al. |
| 2011/0153023 A1 | 6/2011 | Deffenbaugh et al. |
| 2011/0224673 A1 | 9/2011 | Smith |
| 2011/0276144 A1 | 11/2011 | Wirth et al. |
| 2011/0313533 A1 | 12/2011 | Gunther |
| 2012/0109229 A1 | 5/2012 | Forsell |
| 2012/0109321 A1 | 5/2012 | Stone et al. |
| 2012/0123419 A1 | 5/2012 | Purdy et al. |
| 2012/0221111 A1 | 8/2012 | Burkhead, Jr. et al. |
| 2012/0239042 A1 | 9/2012 | Lappin et al. |
| 2012/0253467 A1* | 10/2012 | Frankle ............... A61F 2/40 623/19.11 |
| 2012/0265315 A1 | 10/2012 | Kusogullari et al. |
| 2012/0277880 A1 | 11/2012 | Winslow et al. |
| 2012/0296435 A1 | 11/2012 | Ambacher |
| 2013/0123929 A1 | 5/2013 | McDaniel et al. |
| 2013/0123930 A1 | 5/2013 | Burt |
| 2013/0144393 A1 | 6/2013 | Mutchler et al. |
| 2013/0173006 A1 | 7/2013 | Duport |
| 2013/0178943 A1 | 7/2013 | Duport |
| 2013/0190882 A1 | 7/2013 | Humphrey |
| 2013/0211539 A1 | 8/2013 | McDaniel et al. |
| 2013/0261626 A1 | 10/2013 | Chavarria et al. |
| 2013/0261629 A1 | 10/2013 | Anthony et al. |
| 2013/0261754 A1 | 10/2013 | Anthony et al. |
| 2013/0282129 A1 | 10/2013 | Phipps |

(56) References Cited

U.S. PATENT DOCUMENTS

| | | | |
|---|---|---|---|
| 2014/0012272 A1 | 1/2014 | Leisinger | |
| 2014/0012380 A1 | 1/2014 | Laurence et al. | |
| 2014/0058523 A1 | 2/2014 | Walch et al. | |
| 2014/0107792 A1 | 4/2014 | Hopkins et al. | |
| 2014/0156012 A1 | 6/2014 | Winslow | |
| 2014/0296988 A1 | 10/2014 | Winslow et al. | |
| 2014/0358239 A1 | 12/2014 | Katrana et al. | |
| 2014/0358240 A1 | 12/2014 | Katrana et al. | |
| 2014/0379089 A1 | 12/2014 | Bachmaier | |
| 2015/0134066 A1 | 5/2015 | Bachmaier | |
| 2015/0250472 A1* | 9/2015 | Ek | A61F 2/4606 606/232 |
| 2015/0250601 A1 | 9/2015 | Humphrey | |
| 2015/0289984 A1 | 10/2015 | Budge | |
| 2015/0297354 A1 | 10/2015 | Walch et al. | |
| 2015/0305877 A1* | 10/2015 | Gargac | A61F 2/4081 623/19.11 |
| 2015/0374502 A1 | 12/2015 | Hodorek et al. | |
| 2016/0051367 A1 | 2/2016 | Gervasi et al. | |
| 2016/0157911 A1 | 6/2016 | Courtney, Jr. et al. | |
| 2016/0310285 A1 | 10/2016 | Kovacs et al. | |
| 2016/0324648 A1 | 11/2016 | Hodorek et al. | |
| 2017/0105843 A1 | 4/2017 | Britton et al. | |
| 2017/0273800 A1 | 9/2017 | Emerick et al. | |
| 2017/0304063 A1 | 10/2017 | Hatzidakis et al. | |
| 2017/0367836 A1 | 12/2017 | Cardon et al. | |
| 2018/0092760 A1 | 4/2018 | Sperling et al. | |
| 2018/0271667 A1 | 9/2018 | Kemp et al. | |
| 2019/0105165 A1 | 4/2019 | Sikora et al. | |
| 2019/0105169 A1 | 4/2019 | Sperling | |
| 2019/0175354 A1 | 6/2019 | Knox et al. | |
| 2019/0216518 A1 | 7/2019 | Courtney, Jr. et al. | |
| 2019/0328536 A1 | 10/2019 | Martin et al. | |
| 2020/0008947 A1 | 1/2020 | Emerick et al. | |
| 2020/0121467 A1 | 4/2020 | Hodorek et al. | |
| 2020/0146834 A1 | 5/2020 | Hodorek et al. | |
| 2020/0214845 A1 | 7/2020 | Knox et al. | |

FOREIGN PATENT DOCUMENTS

| | | |
|---|---|---|
| DE | 102004042502 | 3/2006 |
| EP | 0 274 094 | 8/1990 |
| EP | 1 413 265 | 4/2004 |
| EP | 0 959 822 | 5/2004 |
| EP | 1 125 565 | 12/2004 |
| EP | 1 518 519 | 3/2005 |
| EP | 1 004 283 | 5/2005 |
| EP | 1 639 967 | 3/2006 |
| EP | 1 762 191 | 3/2007 |
| EP | 1 752 105 | 7/2008 |
| EP | 1 952 788 | 8/2008 |
| EP | 1 867 303 | 9/2010 |
| EP | 1 977 720 | 1/2011 |
| EP | 2 231 032 | 8/2011 |
| EP | 1 550 420 | 2/2012 |
| EP | 2 363 098 | 9/2012 |
| EP | 2 261 303 | 11/2012 |
| EP | 1 706 074 | 12/2012 |
| EP | 2 564 814 | 3/2013 |
| EP | 2 567 676 | 3/2013 |
| EP | 2 574 313 | 4/2013 |
| EP | 2 616 013 | 7/2013 |
| EP | 2 626 017 | 8/2013 |
| EP | 2 474 288 | 9/2013 |
| EP | 2 663 263 | 5/2014 |
| EP | 2 502 605 | 8/2014 |
| EP | 2 800 541 | 11/2014 |
| EP | 2 815 726 | 8/2015 |
| EP | 2 353 549 | 6/2016 |
| EP | 3 117 801 | 1/2017 |
| EP | 2 965 720 B1 | 7/2017 |
| FR | 2 674 122 | 9/1992 |
| FR | 2997290 B1 | 11/2015 |
| GB | 2405346 | 3/2005 |
| GB | 2406278 | 3/2005 |
| WO | WO 01/67988 | 9/2001 |
| WO | WO 02/17822 | 3/2002 |
| WO | WO 2005/094693 | 10/2005 |
| WO | WO 2008/011078 | 1/2008 |
| WO | WO 2008/146124 | 12/2008 |
| WO | WO 2009/083707 | 7/2009 |
| WO | WO 2011/012318 | 2/2011 |
| WO | WO 2011/081797 | 7/2011 |
| WO | WO 2012/035263 | 3/2012 |
| WO | WO 2012/130524 | 10/2012 |
| WO | WO 2013/009407 | 1/2013 |
| WO | WO 2013/064569 | 5/2013 |
| WO | WO 2013/148229 | 10/2013 |
| WO | WO 2014/005644 | 1/2014 |
| WO | WO 2014/058314 | 4/2014 |
| WO | WO 2014/063197 | 5/2014 |
| WO | WO 2015/112307 | 7/2015 |
| WO | WO 2016/094739 | 6/2016 |
| WO | WO 2017/165090 | 9/2017 |
| WO | WO 2017/184792 | 10/2017 |
| WO | WO 2018/022227 | 2/2018 |
| WO | WO 2019/060780 | 3/2019 |
| WO | WO 2019/106278 | 6/2019 |
| WO | WO 2020/072452 | 4/2020 |
| WO | WO 2020/072454 | 4/2020 |

OTHER PUBLICATIONS

Boileau, et al., "The Three-Dimensional Geometry of the Proximal Humerus: Implications for Surgical Technique and Prosthetic Design," J Bone Joint Surg, Sep. 1997, vol. 79-B, Issue 5, pp. 857-865.

Routman, et al., "Reverse Shoulder Arthroplasty Prosthesis Design Classification System," Bulletin of the Hospital for Joint Diseases, 2015, vol. 73 (Suppl 1), pp. S5-S14.

"Assembly/Disassembly Instructions," Product: CMI Reamer, Tornier, Inc., available as early as Jan. 2013, pp. 1-2.

DePuy Synthes. "Global APG—Design Rationale and Surgical Technique." DePuy Synthes, 2010. Web. Dec. 22, 2014. <http://www.synthes.com/sites/NA/NAContent/Docs/Product Support Materials/Technique Guides/0612-13-509_GlobalAPGdesignrationaleST.pdf>.

"GLOBAL STEPTECH Anchor Peg Glenoid Surgical Technique," DePuy Orthopaedics, Inc., Mar. 2014, pp. 1-32.

International Search Report and Written Opinion for PCT/US2017/038843 dated Aug. 28, 2017 in 17 pages.

Zimmer®. "Trabecular Metal Glenoid—Surgical Technique." 2008, 2009. <http://www.zimmer.com/content/pdf/en-US/Trabecular_Metal_Glenoid_Surgical_Technique_97-4301-204-00_Rev_1_11_2009_US_ONLY.pdf> Last Accessed: May 1, 2014.

Final Rejection issued in connection with U.S. Appl. No. 16/208,956, filed Apr. 30, 2021, 13 pages.

Non-Final Office Action issued in connection with U.S. Appl. No. 17/250,964, filed Jul. 26, 2021, 27 pages.

* cited by examiner

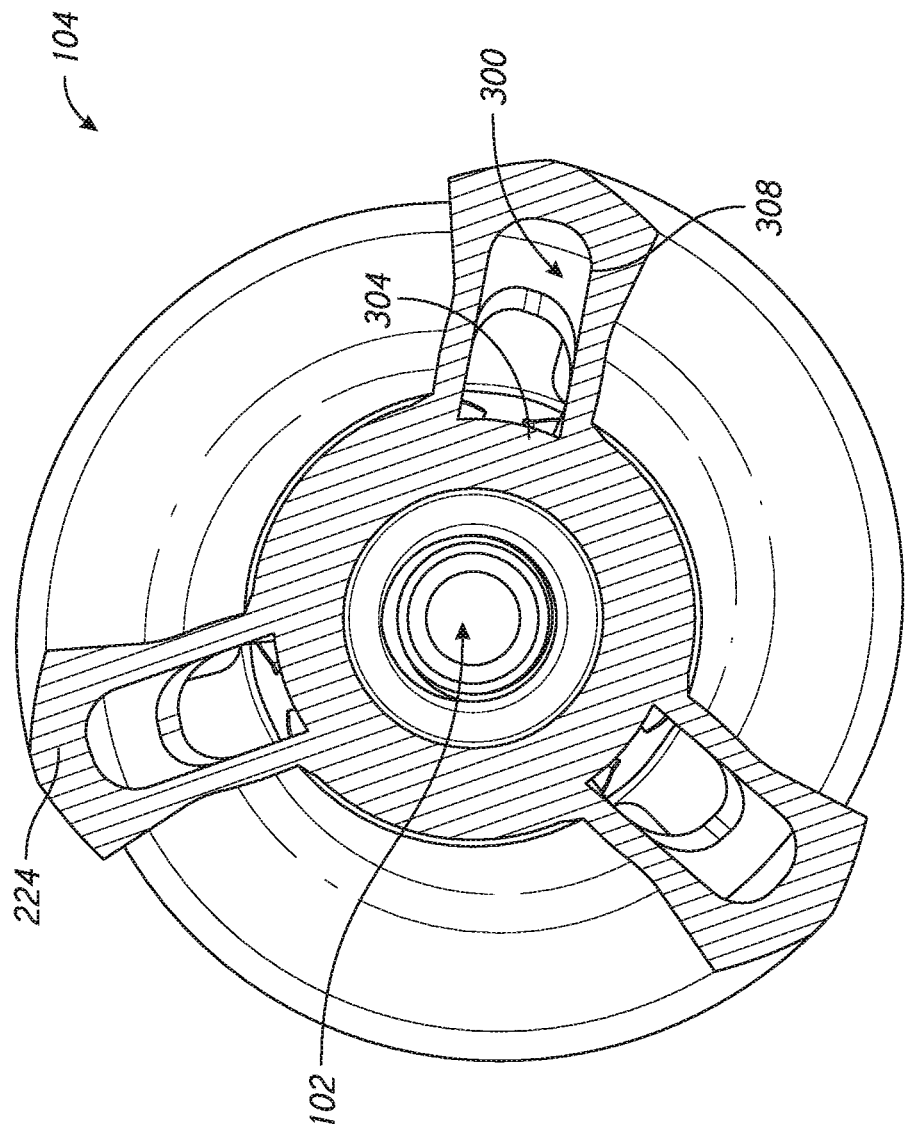

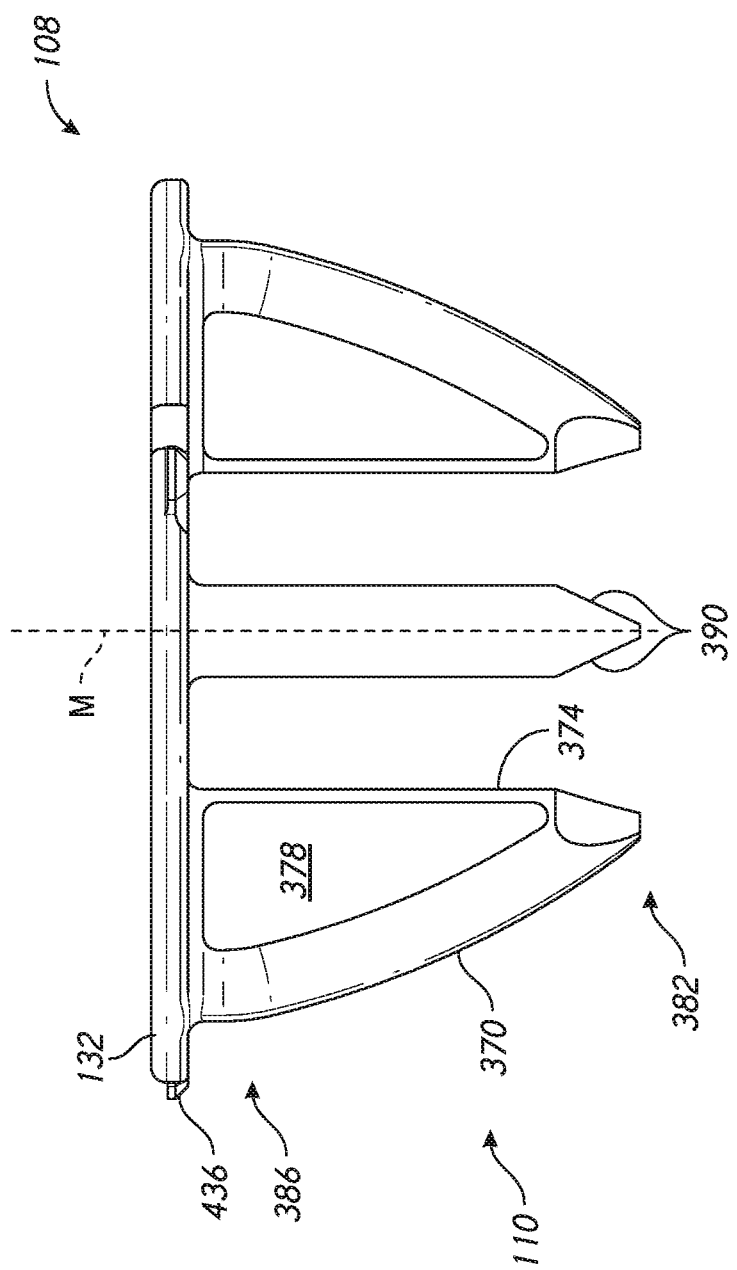

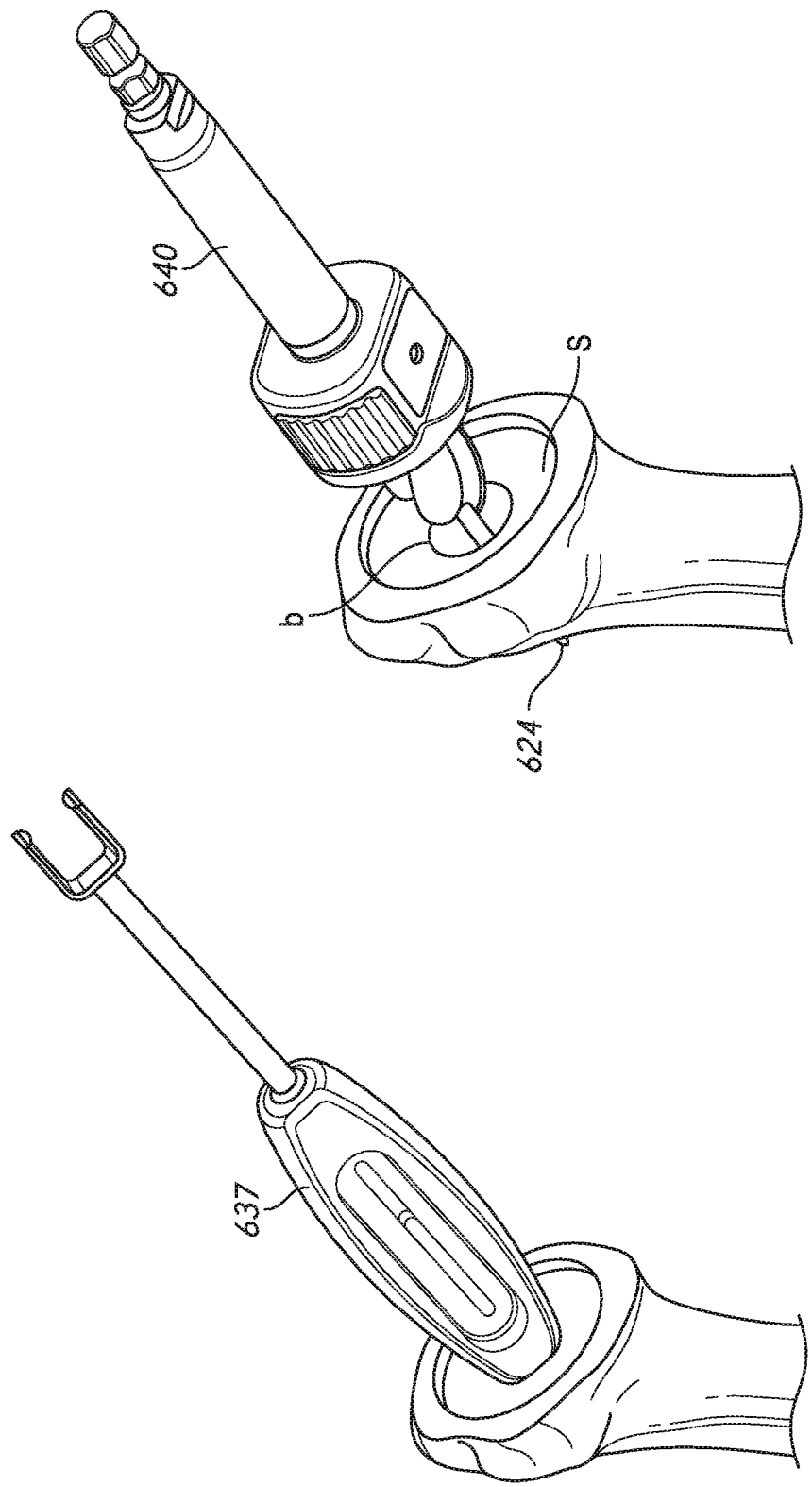

STEMLESS PROSTHESIS ANCHOR COMPONENT

BACKGROUND OF THE INVENTION

Field of the Invention

The present disclosure relates to a stemless prosthesis anchor component of a joint prosthesis.

Description of the Related Art

Skeletal joints have a variety of configurations providing for a wide range of smooth movement of two or more bones relative to each other. For example, in a shoulder joint, the head of the humerus interacts with the glenoid cavity of the scapula in a manner similar to a "ball and socket" joint. Over time, it may become necessary to replace a joint, such as the shoulder joint, with a prosthetic joint. The prosthetic joint can include components mounted to one, two or more than two bones at the joint. For example, the prosthetic joint can include a humeral component, a glenoid component or both a humeral and a glenoid component.

Conventional humeral components include a humeral head jointed to a stem. The stem is configured to be inserted into a medullary canal of the humerus. In certain cases, insertion of the stem disadvantageously requires bone to be removed to fit the stem to the medullary canal due to patient-to-patient anatomical variation. Another disadvantage of this approach is that integration of the stem into the bone through a natural process of bone ingrowth can make it difficult to remove the humeral component if it becomes necessary to replace the humeral component with another device.

A stemless humeral component may be used to address some of the disadvantages of conventional humeral components. Stemless humeral components can decrease the amount of bone loss in preparing the humerus to receive the component and decrease the complexity of the joint replacement procedure.

Stemless humeral component designs can be more challenging to secure to the humerus. Conventional stemless designs rely on bone ingrowth for strength. While such designs perform well over time, there is a risk in the early days and weeks after surgery where such ingrowth has not yet occurred that the stemless humeral component will be dislodged from the humerus. Dislodgement may also occur due to backing out after being inserted, excessive wear, forces applied thereto during a revision surgery or other high load conditions.

SUMMARY OF THE INVENTION

Accordingly, there is a need for additional stemless components or prostheses designed to preserve bone in initial implantation while enhancing initial pull-out and back-out resistance. Preferably enhanced initial dislodgement resistance will also provide excellent long term fixation.

In one embodiment, a shoulder assembly is provided that includes a base member and a locking device. The base member includes a collar, a helical structure, and a first pathway projecting distally of the collar. The helical structure extends from the collar in a distal direction. The first pathway projects distally of the collar and through the helical structure. The first pathway is disposed adjacent to an inner periphery of the helical structure. The first pathway is generally transverse to the helical structure and extending in a space between successive portions of the helical structure. The locking device has a proximal support and a first arm that projects distally of the proximal support. The first arm is configured to be disposed in the first pathway that projects distally of the collar when the proximal support is disposed adjacent to the collar. The first arm is disposed through bone in the space between successive portions of the helical structure when the shoulder assembly is implanted.

In some embodiments, a kit can be provided that includes a shoulder assembly as described above, an anatomic articular component, and a reverse articular component. The anatomic articular component is mateable with the shoulder assembly. The anatomic articular component has a convex articular surface adapted to articulate with a concave surface of or on a scapula of a patient. The reverse articular component is mateable with the shoulder assembly. The reverse articular component comprises a concave articular surface adapted to articulate with a convex surface on a scapula of a patient. The reverse articular component can include a separate tray component for mating an articular surface to the base member.

In another embodiment, a prosthesis assembly is provided that includes a base member that has a helical structure and a first pathway. The base member has a first end and a second end. The helical structure extends between the first end and the second end. The first end comprises a distal or medial end in some applications. The second end comprises a proximal end or a lateral end in some applications. The first pathway is accessible from the second end and is directed toward the first end through the helical structure. The first pathway is located inward of an outer periphery of the helical structure, e.g., adjacent to an inner periphery of the helical structure. The first pathway is generally transverse to the helical structure. The first pathway extends in a space between successive portions of the helical structure. The prosthesis assembly includes a locking device that has a support member and a first arm that projects away from the support member. The first arm is configured to be disposed in the first pathway when the support member is disposed adjacent to the second end of the base member. The first arm is disposed through bone in the space between successive portions of the helical structure when the prosthesis assembly is implanted.

The prosthesis assembly discussed above can be mated with a proximal humerus. The prosthesis assembly discussed above can be mated with other anatomy as well, such as a glenoid of a scapula. The prosthesis assembly discussed above can be mated with a bone adjacent to an elbow joint, such as a distal humerus or a proximal radius. The prosthesis assembly discussed above can be mated with a bone adjacent to a wrist joint, such as a distal radius. The prosthesis assembly discussed above can be mated with a bone adjacent to the hip, such as a proximal femur. The prosthesis assembly discussed above can be mated with a bone adjacent to a knee joint, such as a distal femur or a proximal tibia. The prosthesis assembly discussed above can be mated with a bone adjacent to an ankle joint, such as a distal tibia or a proximal talus In another embodiment, a method of implanting a prosthesis is provided. The method includes advancing by rotation a base member into a bone adjacent to a joint. The bone can include an epiphysis of a humerus of a patient. The bone can include a glenoid of a scapula of a patient. The bone can include a distal portion of a humerus adjacent to an elbow joint. The bone can include a proximal portion of a radius adjacent to an elbow joint. The bone can include a distal portion of a radius adjacent to a wrist joint. The bone can include a proximal portion of a femur adjacent to a hip joint. The bone can include a distal portion of a femur adjacent to a knee joint. The bone can include a proximal portion of a tibia adjacent to a knee joint. The bone can include a distal portion of a tibia adjacent to an ankle joint. The bone can include a proximal portion of a talus adjacent to an ankle joint. The base member comprising a helical structure configured to engage cancellous bone of the epiphysis or other portion of any of the bones set forth above. A locking device is advanced by linear translation into the base member. The locking device has at least one arm adapted to span a gap between adjacent portions of the helical structure. The locking device contacts the cancellous bone in the gap.

In another embodiment, a glenoid assembly is provided. The glenoid assembly includes a base member and a plate member. The base member has a medial end and a lateral end. The base member has a helical structure that extends between the medial end and the lateral end and a first pathway. The first pathway is accessible from the lateral end and is directed toward the medial end. The first pathway can extend through the helical structure and can be located inward of an outer periphery of the helical structure, e.g., adjacent to an inner periphery of the helical structure. The first pathway can be generally transverse to the helical structure and can extend in a space between successive portions of the helical structure. The plate member has a flange and a first arm that projects away from the flange. The first arm is configured to be disposed in the first pathway when the plate member is disposed adjacent to the lateral end of the base member. The first arm is disposed through bone in the space between successive portions of the helical structure when the prosthesis assembly is implanted.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of each of the drawings.

FIG. 3D is a cross-sectional view of the base member of FIG. 2 taken at section plane 3D-3D;

FIG. 4 is a side view of one embodiment of a locking component, which is a component configured to control, e.g., reduce or eliminate and/or control rotation of a base member or of a helical structure of a prosthesis assembly;

FIGS. 8-16 illustrate various methods for implanting a prosthesis assembly of FIGS. 1-7 into a portion of a bone;

DETAILED DESCRIPTION OF THE PREFERRED EMBODIMENT

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Figure 1:
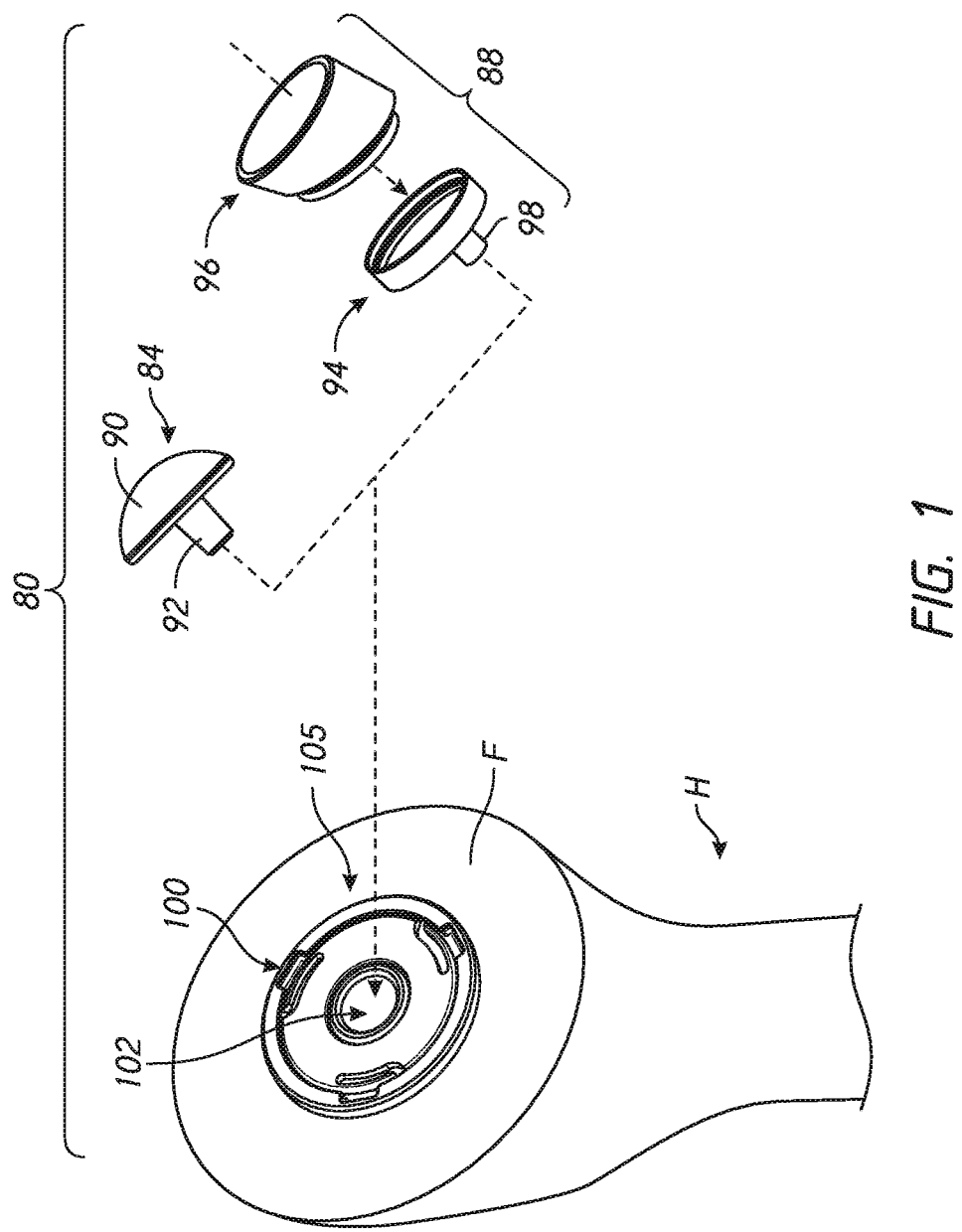
FIG. 1 is a perspective view of one embodiment of a stemless shoulder assembly shown mounted in a humerus, and further illustrating a kit including anatomic and reverse shoulder articular components.
Figure 18B:
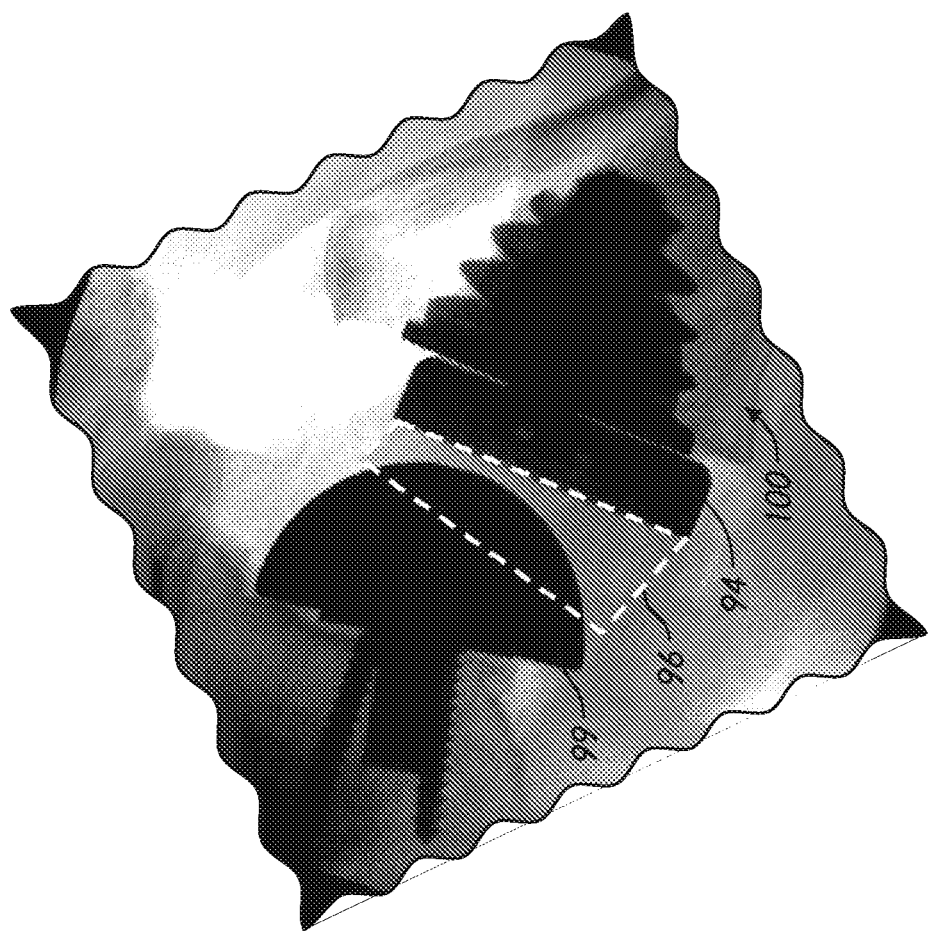
FIG. 18B shows a reverse shoulder prosthesis including a reverse articular component coupled with the humerus and a convex glenoid component, sometimes referred to as a glenoid sphere, coupled with the scapula.

FIG. 1 shows a kit 80 that includes a shoulder assembly 100. The kit 80 can include one or both of an anatomic articular component 84 and a reverse articular component 88. The anatomic articular component 84 can comprise a one-piece structure including a convex articular surface 90 disposed on a proximal or lateral side and a tapered projection 92 disposed on a distal side thereof. The reverse articular component 88 can comprise a two-piece structure including a tray 94 and an insert 96. In other embodiments, the articular component 88 has a one-piece configuration. In other embodiments, the articular component 88 has a monolithic configuration. Monolithic embodiments can comprise a one material configuration. Monolithic embodiments can comprise two or more material. The insert 96 can mate with the tray 94 in any suitable manner, such as by interference fit or snap fit. The tray 94 can include a tapered projection 98. FIG. 18B shows that the kit 80 also can include a glenoid sphere 99 and corresponding components for anchoring the glenoid sphere in a glenoid. The insert 96 is shown in just one embodiment in which the tray is angled, such that a plane intersecting the medial side of the insert 96 is at an angle to the side that faces the shoulder assembly 100 providing a thicker superior portion. In other embodiments the insert 96 is angled, such that a plane intersecting the medial side of the insert 96 is at an angle to the side that faces the shoulder assembly 100 providing a thicker inferior portion. In other embodiments the insert 96 is not angled, such that the plane intersecting the medial side of the insert 96 is substantially parallel to the side that faces the shoulder assembly 100.

FIG. 1 shows the shoulder assembly 100, as further described below in connection with FIGS. 2-7, implanted in an exposed face F of a humerus H. The assembly 100 has a recess 102 in which further components of a prosthetic shoulder joint can be secured. The assembly 100 and the recess 102 enable the humerus H to be fitted with either an anatomical shoulder by receiving the anatomic articular component 84, more particularly, the projection 92 or a reverse shoulder component 88 by receiving the projection 98 either initially or as part of a revision procedure. Methods of using the kit 80 to implant the shoulder assembly 100 as part of a shoulder prosthesis are discussed below in connection with FIGS. 8-16. FIGS. 19-26 show that further embodiments can be used beyond humeral application and beyond shoulder joint procedures. FIG. 27 illustrates the performance of certain embodiments compared to a prior art design. While incremental differences in these embodiments and methods are discussed below, it is to be understood that features of each embodiment can be combined with features of the other embodiments, as appropriate.

I. Humeral Shoulder Assemblies Having Rotation Control Locking Devices

Figure 7:
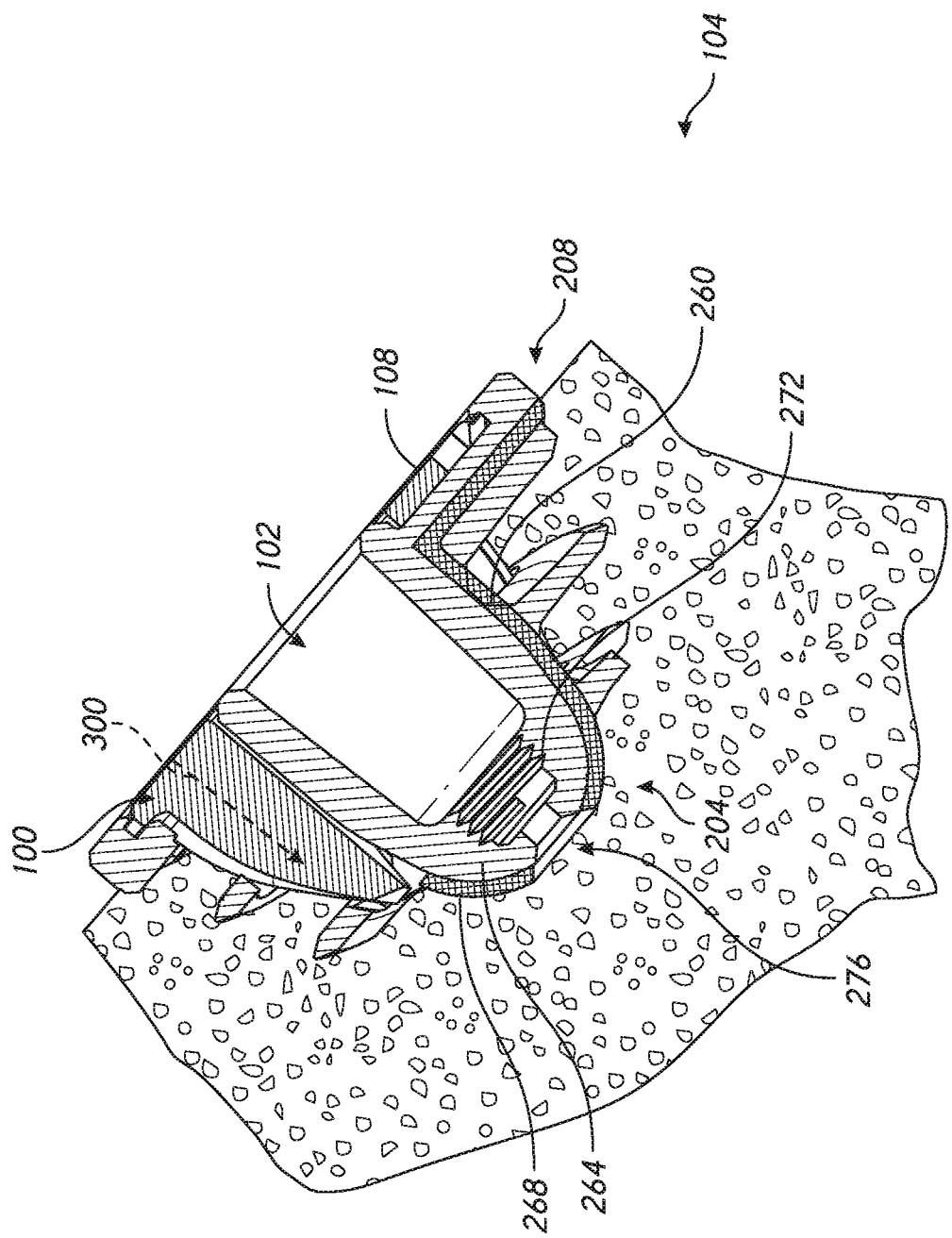
FIG. 7 is a cross-sectional view of the stemless shoulder assembly of FIG. 2 with the assembly disposed in the humeral head.

FIGS. 1 and 7 show the shoulder assembly 100 applied to a shoulder joint. The assembly 100 can provide secure stemless connection to the humerus H. The shoulder assembly 100 provides for simple implantation because a base member thereof can be directly threaded into cancellous bone without being mated to another pre-placed base member. The shoulder assembly 100 can be fully retained within a head h of the humerus H. FIG. 7 shows that the distal-most portion of the assembly 100 preferably can be disposed in the humeral head h. The assembly 100 does not have a stem or other member that protrudes beyond the head h into a medullary canal of the humerus. This approach is less invasive and simpler than procedures involving placement of a stem in a medullary canal. In other embodiments illustrated in part in FIG. 10 by the creation of a recessed surface s having a depth accommodating a thickness of a proximal portion of the assembly 100, the assembly 100 may be recessed within the humeral head of the humerus H such that a proximal face 105 the assembly 100 is flush with respect to a cut surface of the bone.

Figure 2:
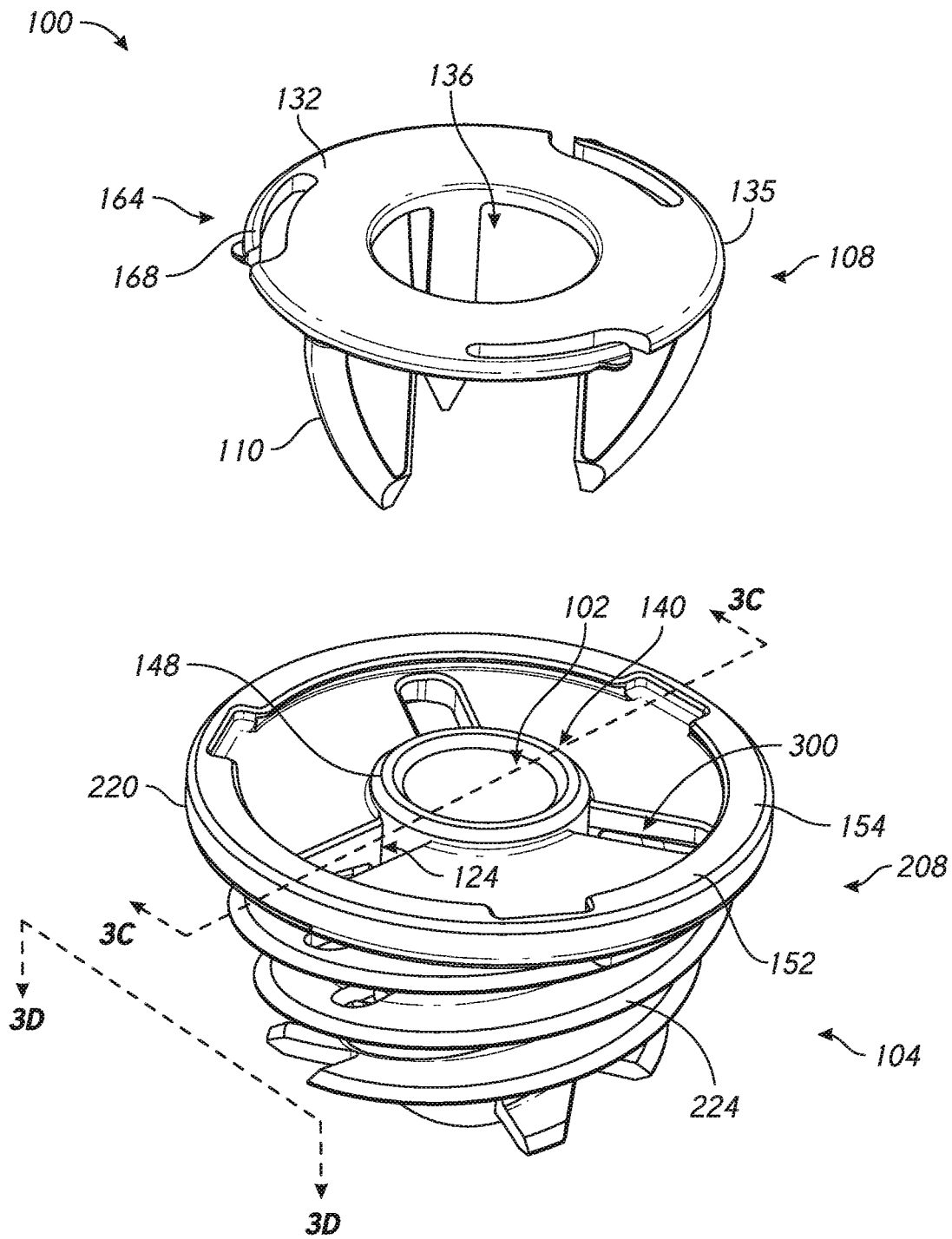
FIG. 2 is an exploded view of the stemless shoulder assembly shown in FIG. 1.

FIG. 2 shows that the assembly 100 includes a base member 104 and a locking device 108. The base member 104 is advanced into a bony structure such as cancellous bone in use. As discussed further below a bone surface may be exposed by resection or reaming, followed by threading of the base member 104 into a newly exposed bone surface. The assembly 100 also includes the locking device 108. The locking device 108 includes a plurality of arms 110. In particular, the arms 110 extend outward or distal from proximal support 132. The arms 110 can include a first arm, a second arm, and a third arm. The arms 110 can be circumferentially spaced equal distances from each other, e.g., about 120 degrees apart in one embodiment. In another variation, the arms 110 include three arms, with two of the three arms spaced 90 degrees from each other and a third arm spaced 135 degrees from one of the other two arms. The locking device 108 may include four or more arms 110. If the arms 110 include four arms, the arms can be circumferentially spaced 90 degrees apart. If the arms 110 include two arms, the arms can be circumferentially spaced 180 degrees apart. The arms 110 are advanced through apertures 124 in the base member 104. In one embodiment, it should be noted that the number of arms 110 corresponds to an equal number of apertures 124. When so advanced, the arms 110 are disposed within the base member 104 in a manner that the arms 110 cross a space between portions, e.g., successive portions, of the base member 100. When so positioned, the arms 110 are also disposed within bone. Thus, two zones of the arms 110 can cross successive or adjacent portions of the base 104 and an intervening portion of the arms 110 can cross bone in a space between the successive or adjacent portion of the base. In this position, the arms 110 control, e.g., resist, rotation of the base member 104 relative to the bone such that the shoulder assembly 100 is secured against backing out of the bone upon implantation.

FIG. 2 also shows that the locking device 108 also includes a proximal support 132. The proximal support 132 is coupled with the arms 110 in a manner discussed further below. The proximal support 132 has a central aperture 136 disposed within an inner periphery thereof and extends outward from the central aperture 136 to an outer periphery 135. The inner and outer periphery of the proximal support 132 are received in a recess 140 formed in the base member 104. In one configuration the recess 140 and the proximal support 132 are configured such that a flush connection is provided between the proximal support 132 and the proximal face of the base member 104. The proximal support 132 can be connected to the base member 104 in an at least partially recessed position in the proximal face of the base member as discussed further below in connection with FIG. 6A.

Figure 3A:
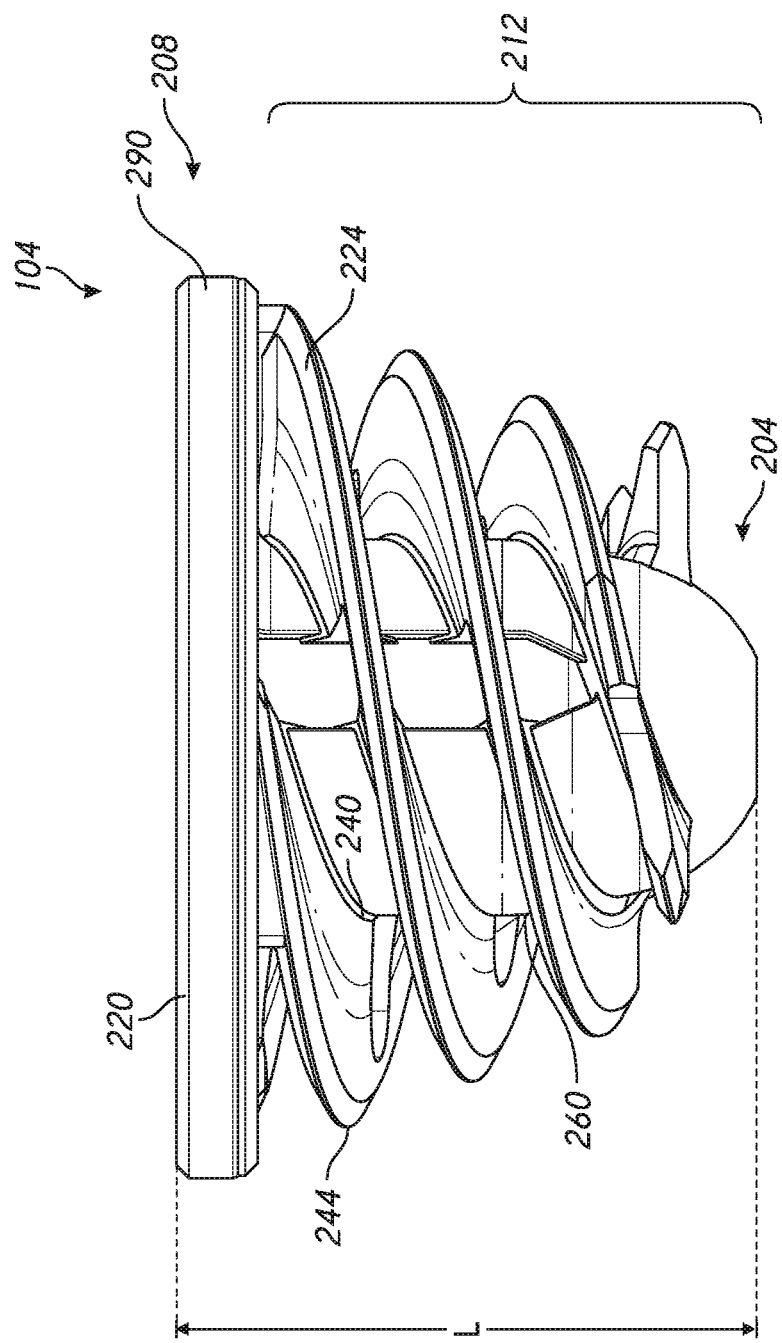
FIG. 3A is a side view of the base member of FIG. 2.
Figure 3B:
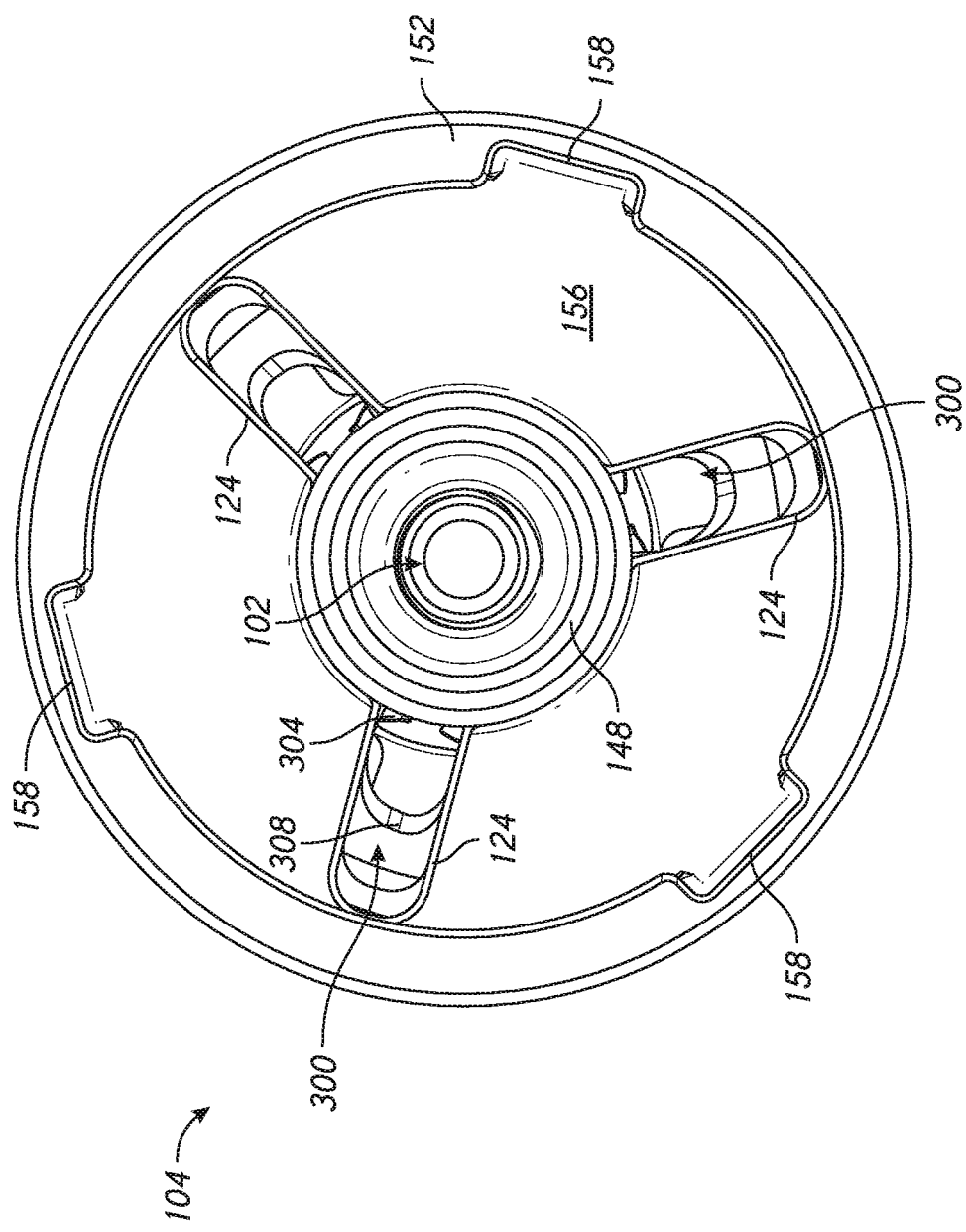
FIG. 3B is a top view of the base member of FIG. 2.

FIGS. 2 and 3B show that the proximal face of the base member 104 can include a raised inner portion 148 and a raised outer portion 152. The outer raised portion 152 extends around an outer periphery 154 of the base member 104. The raised portion 148, 152 are proximally oriented projections relative to a recessed surface 156. The recessed surface 156 can be disposed distally of one or both of the inner portion 148 and the outer portion 152. The raised inner portion 148 can define an aperture for access into the recess 102, which is configured for mating with articular components as discussed below. Each of the raised inner portion and the raised outer portion 148, 152 can comprises annular structures. The recessed surface 156 can comprise an annular portion. The apertures 124 can be formed in the recessed surface 156. In one embodiment the apertures 124 extend radially between the inner raised portion 148 and the outer raised portion 152. The apertures 124 can extend from the inner raised portion 148 to the outer raised portion 152.

The proximal face of the base member 104 also can include a tool interface 158 that enables the base member to be advanced by an inserter into bone, as discussed below in FIG. 14. The tool interface 158 includes three notches in an inward side of the outer raised portion 152. In other embodiments, the tool interface 158 can include apertures in the recessed surface 156, notches in the inner raised portion 148, projections from any surface of the proximal face of the base member 104 or any combination of these features. Also, the tool interface 158 can provide access for a removal tool to engage the locking device 108. As discussed below, the locking device 108 includes a spring arm 168 and a removal tool can be applied at the tool interface 158 to compress the arm 168 to disengage the locking device from the base member 104. In some cases, an inserter tool can engage one or more apertures 124 in the base member 104 upon insertion.

One or more structures for securing the locking device 108 to the base member 104 can be provided as discussed further below. For example the locking device can have an engagement feature 164 disposed on the proximal support 132 that is adapted to engage a corresponding feature on the proximal face of the base member 104. The engagement feature 164 can include an actuatable member that can move into a secure position relative to the recess 140 of the base member 104. As discussed below in connection with FIGS. 5 and 6A, the engagement features 164 can include a spring arm 168 to engage an overhang of the recess 140. As shown in FIG. 2, one embodiment comprises a plurality of actuatable members, e.g., a plurality of spring arms 168. The spring arms 168 can be spaced apart, e.g., providing equal angle separation between adjacent spring arms 168. In one embodiment, the number of spring arms 168 matches the number of arms 110. Each spring arm 168 can be spaced apart from each arm 110 as discussed further below.

In another embodiment, a serration 172 is provided between the arms 110 of the locking device 108 and the base member 104 as discussed in greater detail below in connection with FIG. 6B. The serration 172 is an example of a one-way connection that can be provided between the arms 110 and the base member 104. Other one-way connections can be provided in addition or in place of the serration 172, such as a ratchet, a barb, or one or more spring arms.

FIGS. 2-3B show further details of embodiments of the base member 104. In some embodiments, the base member 104 can include various features described in PCT publication WO2016/094739, the entirety of which is hereby incorporated by reference herein. The base member 104 has a first end 204, a second end 208 and a body 212 that extends between the first end 204 and the second end 208. The base member 104 can comprise a length L between the first end 204 and the second end 208 that is less than a dimension of an articular surface of typical epiphysis to a medullary canal of a typical humerus. As such, the first end 204 can be disposed within the epiphysis when the second end 208 is at a surface of the bone, as shown in FIG. 7. The second end 208 can be disposed at or on a superior medial resection plane of a humerus while the first end 204 is well within the epiphysis. This enables the first end 204 to stop short of a medullary canal of the humerus when the base 104 is fully implanted, which allows the bone between the first end 204 and the medullary canal to remain unaltered and also simplifies the procedure to the extent that any normal access to and preparation of the medullary canal is not needed. In various embodiments, the length L can be between about 15 mm and about 30 mm, between about 18 mm and about 25 mm, between about 18 mm and about 24 mm, between about 21 mm and about 27 mm, between about 24 mm and about 29 mm. The length L can be about 18 mm, about 21 mm about 23 mm, about 24, mm about 26 mm and about 29 mm. In one approach, at least a portion of the assembly 100 is patient specific. For example, the length L can be defined for a specific patient based on pre-operative planning, such as using two dimensional or three dimensional imaging. The base member 104 can thereafter be manufactured for that patient based on the determined dimension L.

The base member 104 can include a collar 220 and a helical structure 224. The helical structure 224 is disposed about a cylindrical portion 260 of the body 212 of the base member 104. In some embodiments, the helical structure 224 extends directly from the body 212 and may be considered threads of the body 212. The helical structure 224 can include one or a plurality of threads, e.g., two, three, four, or more threads, disposed between the first end 204 and the second end 208. The threads can start adjacent to the first end 204 and extend toward, e.g., entirely to the second end 208. FIG. 3A shows that the threads or other helical structure 224 can end at or adjacent to the collar 220. The threads or other helical structure 224 can have inner portions 240 disposed at or on the body 212 about the recess 102 and outer portions 244 disposed along the periphery of the base 104. FIG. 3A shows that the helical structure 224 has a width defined as the distance between the inner and outer portions 240, 244 that is large, e.g., comprising more than one-quarter of, e.g., about one-third of, the width of the base 104 at a given location. These large threads or other helical structure 224 ensure large purchase in the bone. Large purchase provides strong resistance to pullout even prior to any bone ingrowth into the surfaces of the shoulder assembly 100. Generally one or more surfaces of the shoulder assembly 100 that are in direct contact with bone may be textured e.g., coated or layered with a porous material in order to accelerate tissue ingrowth such as bony ingrowth Therefor good initial resistance to pull-out is advantageous for the patient. At least one turn of a thread or other helical structure 224 completely surrounds the recess 102, e.g., by completely surrounding the body 212, in some embodiments.

The body 212 surrounds the recess 102, which is configured to mate with an articular component, such as humeral head or a glenoid sphere. In one embodiment, the body 212 includes a cylindrical portion 260 within which the recess 102 is disposed. The cylindrical portion 260 can have any suitable outside configuration, such as including a textured surface that is well suited to encourage bony ingrowth. The cylindrical portion 260 can include a generally tapered profile in which a portion at or adjacent to the first end 204 of the base member 100 has a first width and a portion at or adjacent to the second end 208 of the base member 100 can have a second width, the second width being greater than the first width. In some embodiments, the cylindrical portion 260 is generally rounded and formed a blunt but tapered profile. The cylindrical portion 260 can have a flat distal surface in some embodiments.

FIG. 7 shows that the cylindrical portion 260 can include a plurality of layers. For example, an inner layer 264 can be disposed adjacent to the recess 102. The inner layer 264 can include the surface surrounding the recess 102 and can extend away from that surface toward an outer surface of the cylindrical portion 260. In one embodiment an outer layer 268 can be disposed adjacent to the outer surface of cylindrical portion 260. The outer layer 268 can extend from the external surface of the cylindrical portion 260 toward the recess 102. In one embodiment, the outer layer 268 is formed directly on the inner layer 264 although other arrangements are possible as well. The outer layer 268 can be a porous structure that is suitable for bony ingrowth.

FIG. 7 also shows that a tool interface 272 can be disposed at or adjacent to the first end 204 of the base member 104. The tool interface 272 can include a threaded portion that can mate with a delivery tool, as discussed further below. A lumen 276 can be provided at the first end 204 such that access can be provided from the first end 204 through the wall of the cylindrical portion 212 into the recess 102. The lumen 276 and recess 102 together provide access for a K-wire or other guiding device such that implanting the base member 104 can be controlled in an appropriate manner.

Figure 6A:
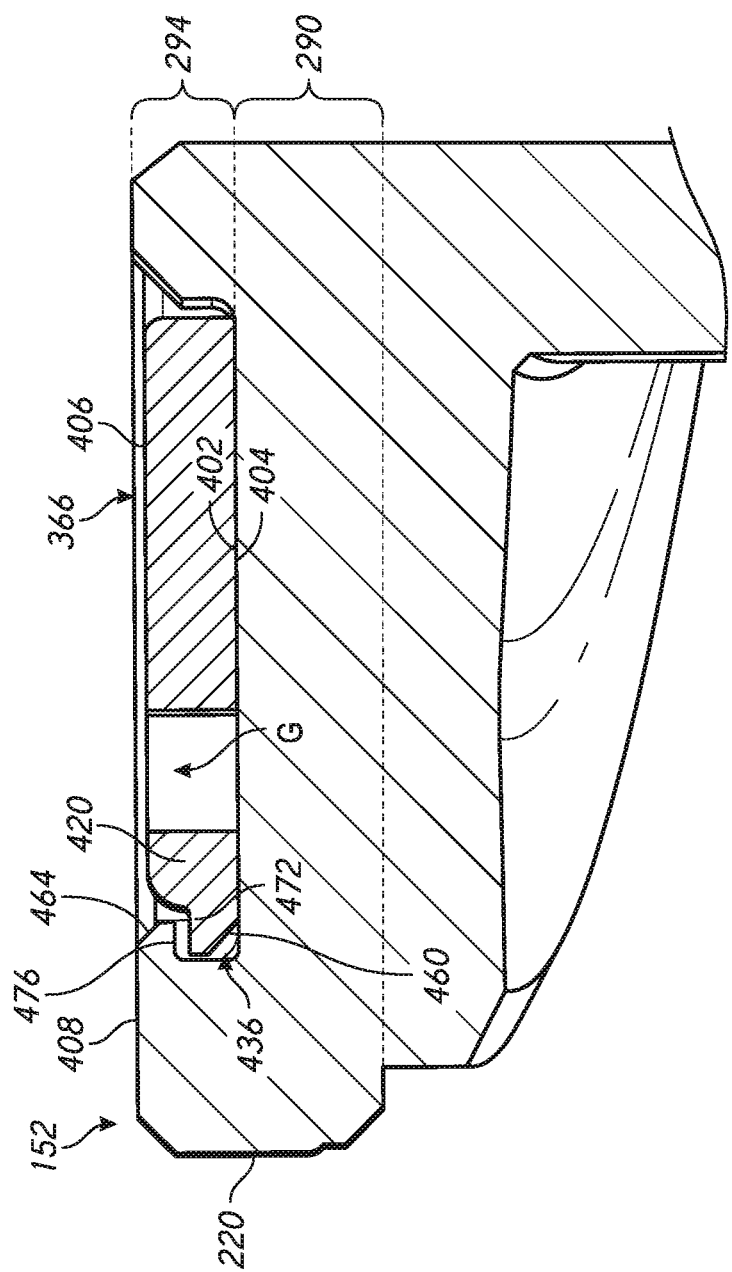
FIG. 6A is a detail view of one embodiment of an engagement feature that causes the locking component of FIG. 4 and the base member of FIGS. 3A and 3B to be engaged.

The collar 220 can be disposed at or can comprise the second end 208 of the base member 104. The collar 220 can have a transverse width, e.g., a diameter that is suitable for a given condition. For example, the diameter of the collar 220 can be selected such that the entire outer periphery of the base 104 is within the bone exposed by resection and/or recessed into such an exposed bone portion, e.g., as illustrated in FIGS. 8-12. In some embodiments the collar 220 has a diameter of more than about 25 mm and less than about 60 mm. The collar 220 can have a diameter of between about 30 mm and about 45 mm. The collar 220 can have a diameter of about 33 mm in one embodiment. The collar 220 can have a diameter of about 42 mm in one embodiment. Making the collar 220 as large as possible within such bounds provides for better load transfer between the collar 220 and the humerus H. In one approach, the diameter of the collar 220 can be defined for a specific patient based on pre-operative planning, such as using two dimensional or three dimensional imaging. The base member 104 can thereafter be manufactured for that patient based on the determined diameter of the collar. For example, the diameter of the collar 220 can be selected such that the collar covers the cortical rim exposed by resection. The collar 220 can attach to or can be integrally formed with the cylindrical portion 260 of the body 212. In one embodiment the collar 220 comprises a transverse flange 290 that extends outward of the recess 102 that is also disposed at the second end 208. An inner portion of the flange 290 can be disposed adjacent to the recess 102 and can include the inner raised portion 148. An outer portion of the flange 290 can be disposed outward of the inner portion. The flange 290 can define the proximal face of the base member 104. The flange 290 can accommodate the proximal support 132 of the locking device 108. FIG. 6A shows that in some embodiments, the flange 290 can at least partially surround a space 294 disposed therein to receive a portion of the locking device 108. The space 294 can be an annular recess located proximal of the recessed surface 156 and between the inner portion 148 and the outer portion. The space 294 can be bounded by an inner edge of the outer portion 152 and an outer edge of the inner portion 148. The flange 290 can engage the spring arm 168 of the locking device 108 in the space 294 such that the locking device 108 will not be inadvertently disengaged from the base 104 and protrude from or be removed from the space 294.

Figure 3C:
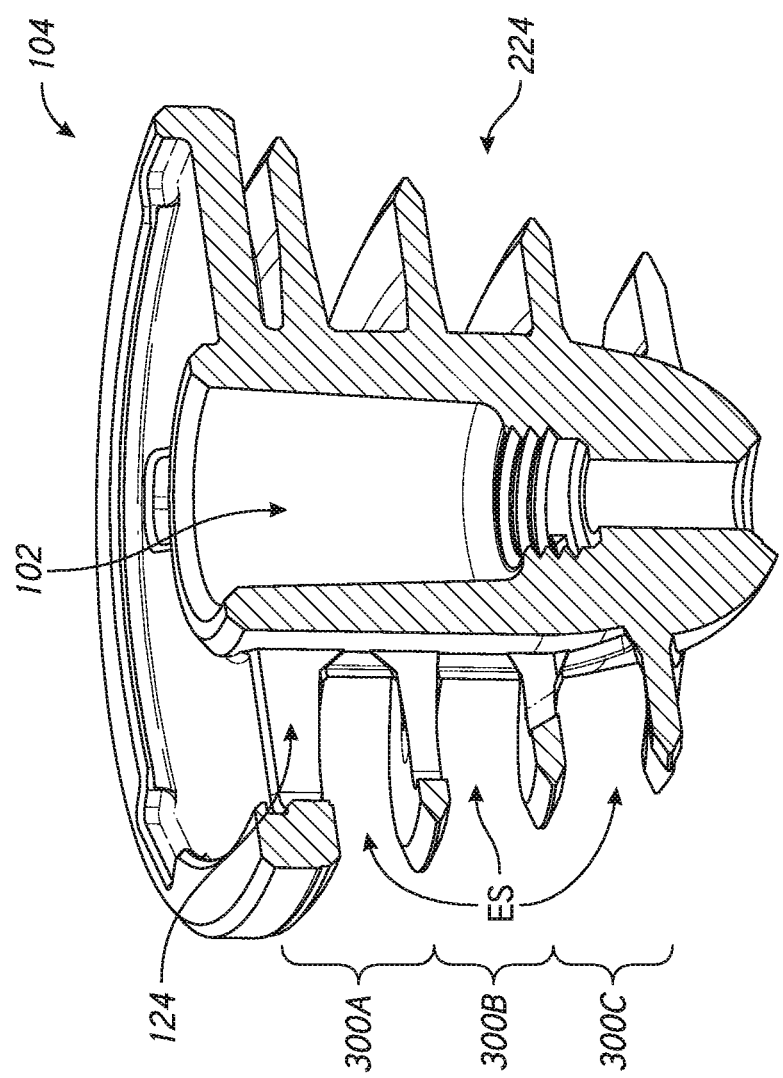
FIG. 3C is a cross-sectional view of the base member of FIG. 2 taken at section plane 3C-3C.

FIGS. 2 and 7 show that in some embodiment, the shoulder assembly 100 includes a pathway 300 that projects distally of the collar 220. The pathway 300 can comprise a first pathway. The shoulder assembly 100 can include a plurality of pathways, 300 with each pathway corresponding to an arm 110 of the locking device 108. FIG. 3B shows that the base 104 can define a plurality of such pathways, e.g., two or three pathways configured to receive corresponding arms 110. There can be four or more than four pathways 300. The pathway 300 can have a first end located at the opening or apertures 124 in the collar 220. The pathway 300 can continue down through the base member 104. FIG. 3C shows that the pathway 300 can have one or more segments disposed through the helical structure 224. A first segment 300A of the pathway 300 extends from the aperture 124 to a first portion, e.g., a proximal-most turn or portion of the helical structure 224 immediately distal of the collar 220, e.g., immediately distal of one of the apertures 124. A second segment 300B of the pathway 300 extends from the first segment 300A to a second turn or portion of helical structure 224 immediately distal of the first portion of the helical structure. A third segment 300C of the pathway 300 can extend from the second segment to a third turn or portion of helical structure 224 immediately distal of the second portion of the helical structure 224.

FIGS. 3A and 3D illustrate that at specific locations along the length of the base 104 from the first end 204 to the second end 208, the pathway 300 can have a first boundary 304 corresponding to an outer surface or layer of the cylindrical portion 260, for example corresponding to a surface of the outer layer 268. The pathway 300 can have a second boundary 308 at a same location along the length of the base 104 from the first end 204 to the second end 208 formed by an adjacent portion of helical structure 224. The second boundary 308 can include a U-shaped opening in the inner portion 240 of the helical structure 224. The U-shaped opening in the inner portion 240 can extend across the width of the helical structure toward the outer portion 244 of the helical structure 224. The U-shaped opening can extend 25%, 35%, 45%, 50%, 60%, 70%, 75% or up to 90% of the distance across the width of the helical structure 224 from the inner portion 240 toward the outer portion 244. In one embodiment, the helical structure 224 has a tapered configuration in which transverse distance between opposite sides of the helical structure 224 is decreased in the direction of the first end 204 compared to the same dimension toward the second end 208. The length of the U-shaped opening in successive portions of the helical structure 224 in the direction toward the first end 204 is progressively less in some embodiments. As a result the width bounded by a turn of the helical structure 224 and the cylindrical portion 260 in the first segment 300A of the pathway 300 can be greater than the width bounded by a turn of the helical structure 224 and the cylindrical portion 260 in the second segment 300B. The width in the second segment 300B can be greater than the width in the third segment 300C bounded by a turn of the helical structure 224 and the cylindrical portion 260. This configuration is advantageous in accommodating embodiments of the locking device 108 having arms 110 that are tapered as discussed further below.

The pathway 300 can extend through one or more spaces between adjacent threads of the helical structure 224. The pathway 300 can comprise two or more segments surrounded by portions of the base member 104 and at least one exposed segment ES. The exposed segments comprise portions of the first and second segments 300A, 300B and between the second and third segments 300B, 300C in some embodiment. The exposed segments ES are exposed in that, unlike the segments 300A, 300B, 300C, the exposed segments of the pathway 300 are not enclosed circumferentially and thus bone disposed within the helical portion 224 can directly contact the arms 110 in the exposed segment. As such the pathway 300 is bounded by bone matter in the exposed segments.

Figure 5:
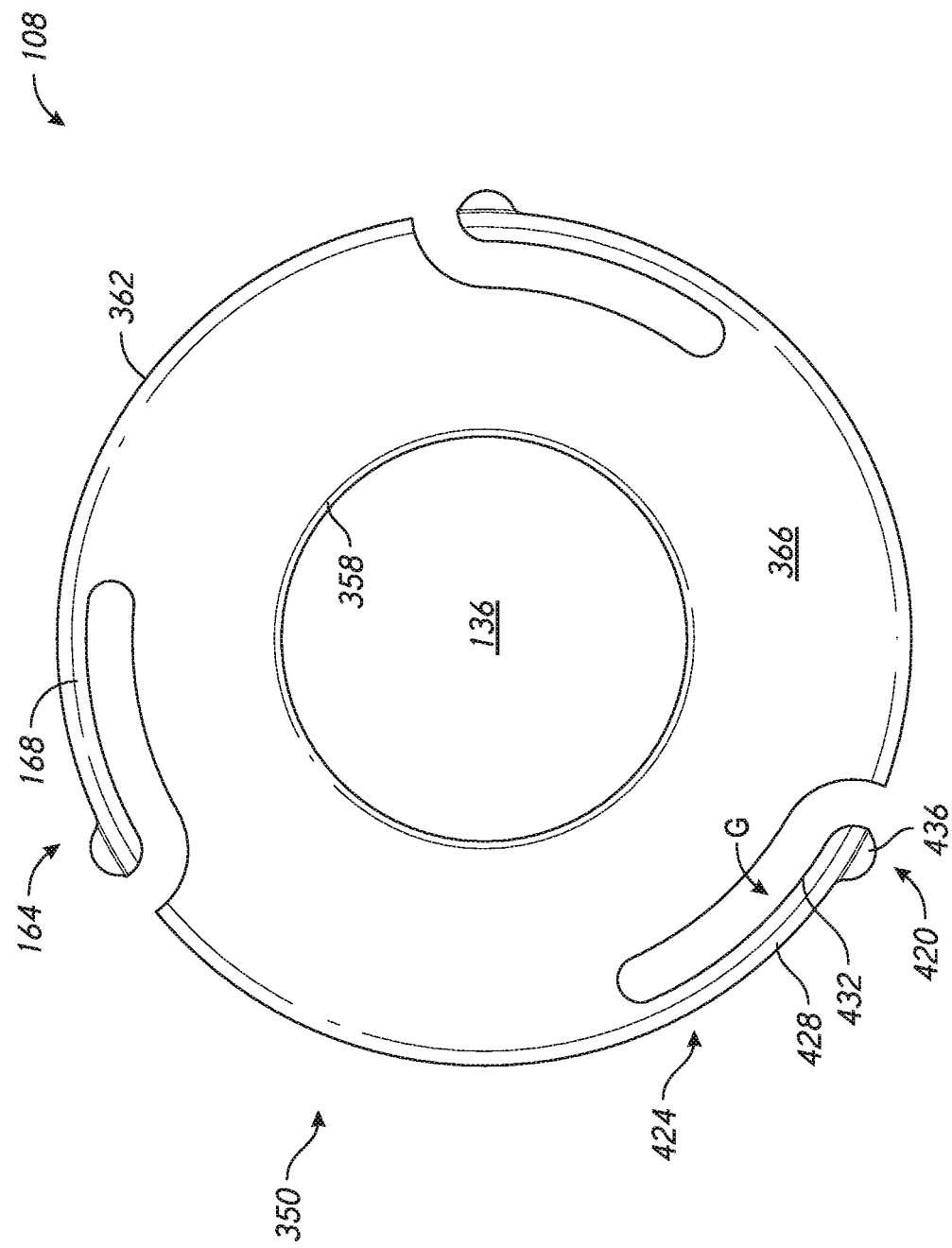
FIG. 5 is a top, proximal side, or medial side view of the locking component of the FIG. 4.

FIGS. 2, 4 and 5 show the locking device 108 in detail. As discussed above, the locking device 108 has a proximal support 132 and a first arm 110 that projects distally of the proximal support 132. The proximal support 132 includes an inner periphery 358, an outer periphery 362 and an annular member 366 disposed therebetween. The inner periphery 358 surrounds the central opening 136, which is sized to receive the inner raised portion 148 of the base member 104 if present. The annular member 366 is configured to be received in the recess 140, as discussed above.

The first arm 110 is configured to be disposed in the first pathway 300. The pathway 300 projects distally of the collar 220. The first arm 110 is disposed distal of the collar 220 when the proximal support 132 is disposed adjacent to a proximal side of the collar 220 and the first arm 110 is in the first pathway 300.

The first arm 110 includes an outer edge 370, an inner edge 374 and a span 378 disposed therebetween. The first arm 110 includes a first end 382 disposed away from the support 132 and a second end 386 disposed adjacent to and in some cases directly coupled to the support 132. The first arm 110 can be tapered, for example with the outer edge 370 approaching the inner edge 374 in the direction toward the first end 382 and/or with the outer edge 370 diverging away from the inner edge 374 in the direction toward the second end 386. In one embodiment, opposite faces 390 of the span 378 are also tapered with at least one of, e.g., both of, the opposite faces 390 approaching a longitudinal mid-plane M of an arm 110. The tapering of the arms between the edges 370, 374 facilitates providing a tapered profile in the base member 104. The tapering of the arms between the edges 370, 374, sometimes referred to herein as a radial taper, facilitates insertion of the first end 382 into the aperture 124 because the first end 382 is much narrower in the dimension between the edges 370, 374 than the aperture 124 is in the radial direction. The tapering of the arms 110 between the faces 390, sometimes referred to herein as a circumferential taper, facilitates insertion of the first end 382 into the aperture 124 because the first end 382 is much narrower in the dimension between the faces 390 than the aperture 124 is in the circumferential direction.

At least one of the circumferential and radial tapers of the arms 110 enables the locking device 108 to easily be advanced through bone matter that is disposed along the pathway 300.

As discussed above, the first arm 110 is disposed through bone in the space between successive portions of the helical structure 224, e.g., in the first segment of the path 300 and in the second segment of the path 300, when the humeral shoulder assembly is implanted. The span 378 and/or other parts of the arms 110 can be porous to enhance bony ingrown when the assembly 100 is implanted. The porous properties can be provided by a porous metal surface or structure or by other porous layers disposed on an underlying layer of metal or another material. At least the widening of the arms 110 toward the second end 386 increases the purchase of bone in the widened area, e.g., in the first segment of the path 300 and also in the second segment of the path 300 compared to an arm that is not tapered.

In some embodiments, the arms 110 are not tapered in the radial direction. For example the arms 110 can have a constant radial dimension between the edges 370 and 374 at a length between, e.g., along the entire length between, the first end 382 and the second end 386. In some embodiments, the arms 110 are not tapered in the circumferential direction. For example the arms 110 can have a constant circumferential dimension between the first end 382 and the second end 386.

As discussed above, the locking device 108 facilitates retaining the base member 104 in the bone at least by opposing, and in some cases completely preventing, rotation of the base member that would cause the base member to back out of the bone into which it has been advanced. Additionally, in some embodiments, it is beneficial to oppose, and in some cases completely prevent, axial movement of the locking device 108 away from the base member 104. At the extreme, such movement could result in the arms 110 of the locking device 108 completely coming out of the pathways 300 and, indeed, out of the base member 104 completely. It also may be desirable to prevent even lesser movements of the locking device 108 relative to the base member 104. As shown in FIG. 6A, a distal face 402 of the annular member 366 may be positioned in direct contact with a proximal face 404 of the transverse flange 290. Such contact can correspond to a proximal face 406 of the annular member 366 being distal of a proximal face 408 of the raised outer portion 152. By recessing the annular member 366, the interaction of the assembly 100 with the articular member of the kit 80 of FIG. 1 is controlled. For example, the annular member 366 will not impede advancement of the articular members into secure engagement with the recess 102.

FIGS. 5 and 6A illustrate various embodiments of axial locking configuration that can be provided in the shoulder assembly 100. An axial locking configuration can include the engagement feature 164 disposed on the proximal support 132. The spring arm 168 of the engagement feature can include a first end 420 disposed away from the annular member 366 and a second end 424 coupled with the annular member 366. The spring arm 168 also has an elongate portion 428 that extends between the first end 420 and the second end 424. The elongate portion 428 preferably has an arcuate form and can, in some embodiments, have the same curvature as a portion of the annular member 366 adjacent to the second end 424. The elongate portion 428 can be separated from the annular member 366 along a radially inner edge 432 of the elongate portion 428 by a gap G. The gap G and the length of the elongate portion 428 can be such that the first end 420 can be moved sufficiently to allow for a snap-fit connection as discussed further below. In one embodiment, the first end 420 of the spring arm 168 has a deflector 436 that facilitates movement of the elongate portion 428 and specifically movement of the first end 420. FIG. 6A shows that the deflector 436 can include an angled surface 460 that initially engages a corresponding angled surface 464 on the base member 104, e.g., on the raised outer portion 152 at the proximal face of the base member. As the arms 110 of the locking device 108 are advanced into the paths 300, the annular member 366 eventually is received in the space 294. At that time, the angled surfaces 460, 464 engage each other, which engagement causes the deflection of the first end 420 of the spring arm 168. The first end 420 is deflected radially inwardly such that the gap G is reduced at least at the first end 420. This allows a proximal facing surface 472 to move to a position distal of a distal facing surface 476. After the proximal facing surface 472 is at a position distal of the distal facing surface 476, the spring arm 168 resiliently moves the deflector 436 back to the configuration shown in FIG. 5. At this point, the proximal facing surface 472 is distal of and aligned with, e.g., positioned under, the distal facing surface 476, as shown in FIG. 6A. In this configuration, the proximal facing surface 472 blocks the distal facing surface 476 from moving proximally. Thus the surfaces 472, 476 prevent the locking device 108 from disengaging from the base member 104.

Another advantageous aspect of the assembly 100 is that the locking device 108 can be quickly and easily disengaged from the base 104. The tooling interface 158 allows an extraction tool to be disposed between the raised outer portion 152 and the spring arm 168. The extraction tool can apply a radially inward force on an outer periphery of the elongate portion 428 of the spring arm 168. Compression of the spring arm 168 decreases the gap G as the proximal facing surface 472 is moved radially inward of the distal facing surface 476. Once the first end 420 is entirely radially inward of the distal facing surface 476, the engagement feature 164 is disengaged from the base 104. If more than one spring arm 168 is provided some or all of the spring arms can be compressed to allow the locking device 108 to be withdrawn from the base 104.

Figure 6B:
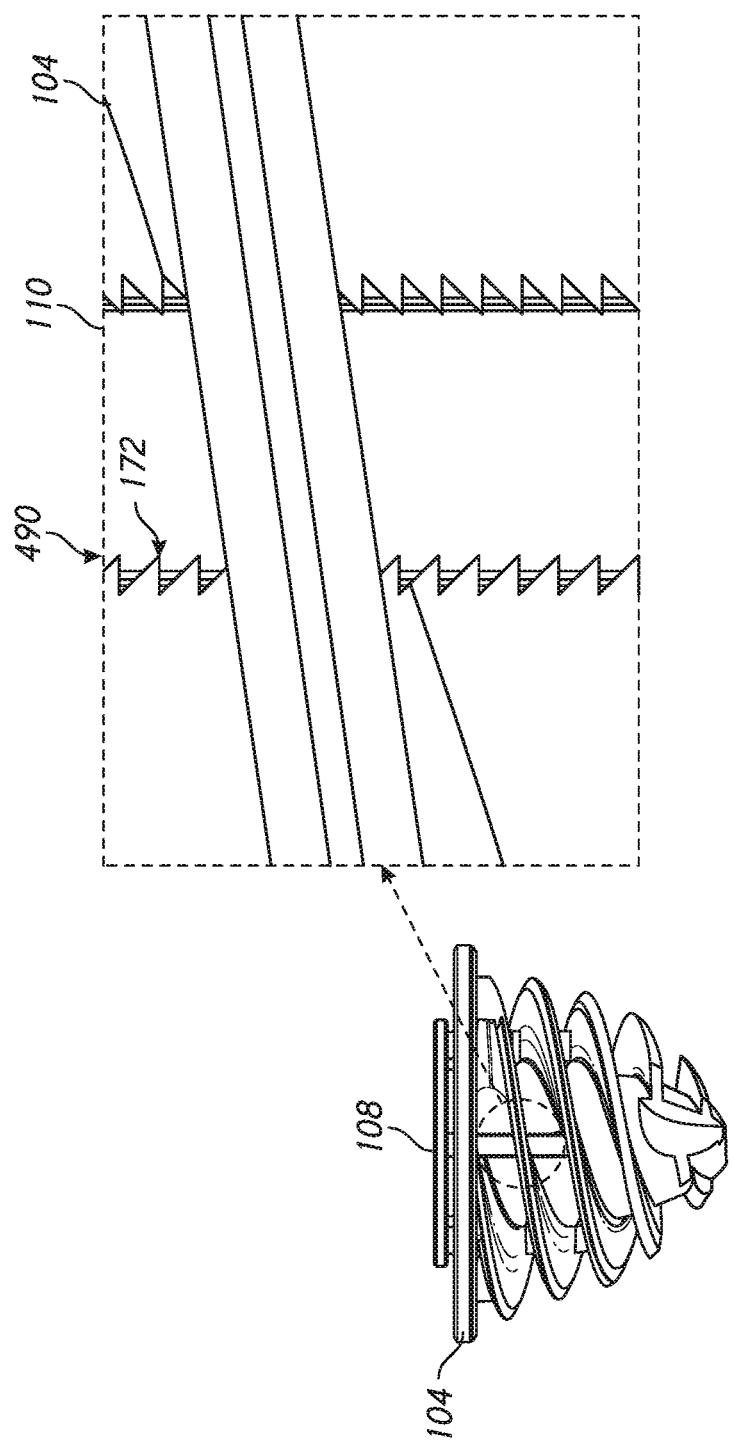
FIG. 6B is a detail view of another embodiment of an engagement feature that causes the locking component and the base member to be engaged at a location within the helical structure.

FIG. 6B shows additional axial locking configurations that can be provided in the shoulder assembly 100. In these embodiments, axial locking can occur at an interface 490 between one or more of the arms 110 and one or more of the pathways 300. For example, the serrations 172 discussed above can be provided at the interface. In one variation, serrations 172 are disposed along the pathway, e.g., on a surface of the cylindrical member 212 and/or on a surface of the helical structure 224. The serrations 172 can be placed at both the surface of the cylindrical member 212 and at the helical structure 224. In another embodiment, the serrations 172 could be provided on a surface of the arm 110, e.g., on one of the outer edge 370, the inner edge 374, and/or on one of the faces 390. The serrations 172 allow for relatively easy insertion of the arms 110 but bite into and oppose withdrawal of the locking device 108 to oppose axial disengagement of the locking device 108 from the base member 104.

The serrations 172 can be disposed along the entire length of the interface between the arms 110 and the base member 104 or just at a position where the base member 104 and the locking device 108 are fully engaged.

II. Method of Application to an End Portion of a Long Bone

FIGS. 8-16 illustrate various techniques for implanting the shoulder assembly 100 in a humerus H. The method illustrates placement in a proximal end of the humerus H, e.g., in the humeral head h.

Figure 8:
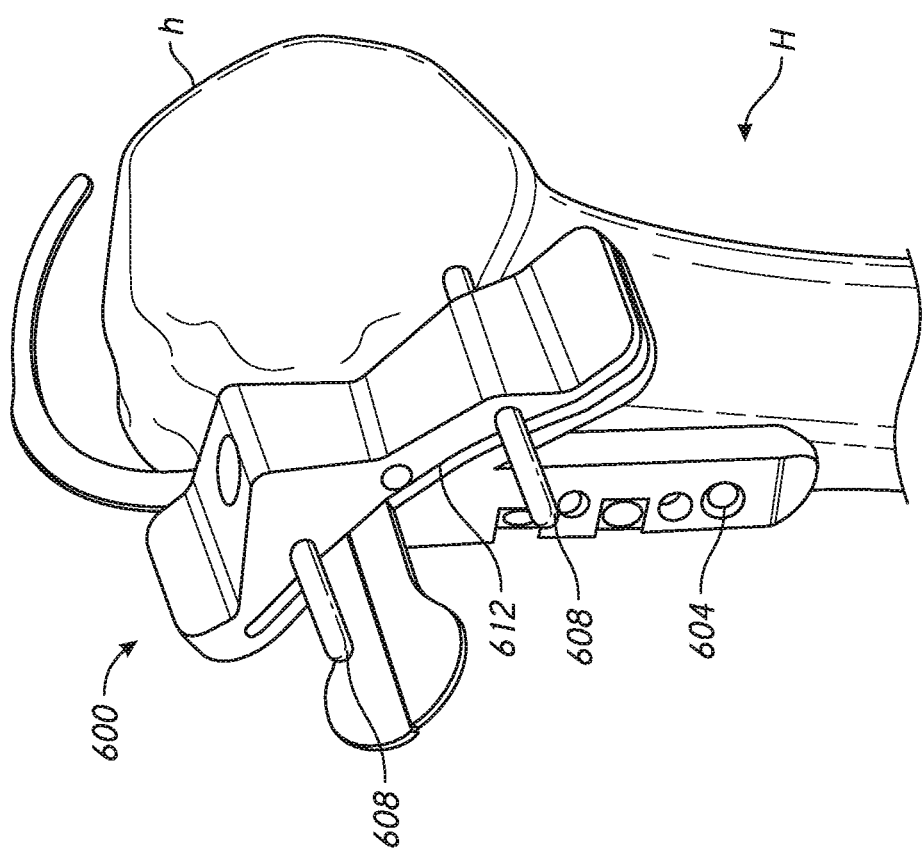
Figure 9:
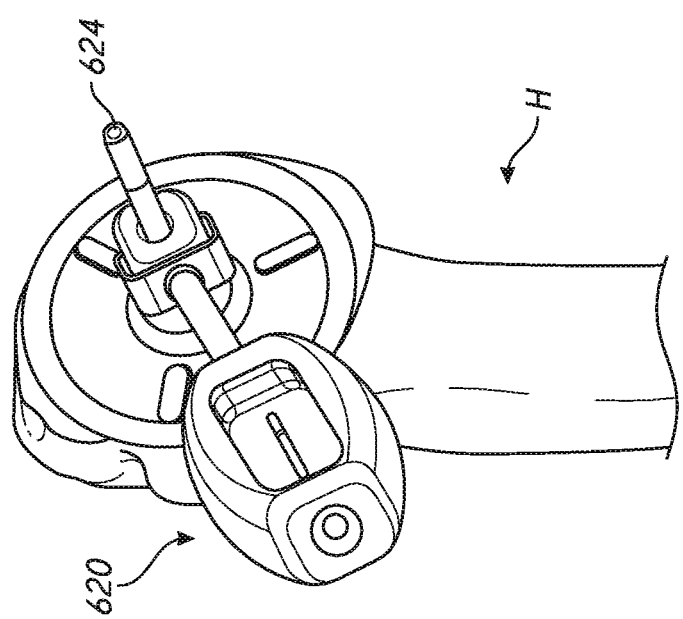

FIG. 8 illustrates an early step of one embodiment of a method including resecting the head h of the humerus H. Prior to resecting the head h of the humerus H a guide 600 is applied to the humerus H. The guide 600 includes structure for mating with the humerus H and the head h, for example, a plate 604 to mate with the humerus H and pins 608 to mate with the head h. The guide 600 also has a slot 612 to guide a saw to cut the humerus H to expose cancellous bone of the head h. FIG. 9 shows that after resecting the head h of the humerus H the size of the head is evaluated with a template 620. To obtain a quick and accurate sizing, a guide pin 624 is first placed in the resected head h. The template 620 is advanced over the guide pin 624 into contact with the resected head. The size of the resected head h is determined from the template 620. The guide 600 can be a reusable guide that is not specific to any particular patients. In other embodiments, the guide 600 is formed with reference to a specific patient. That is, the guide 600 can be formed to mate with the patient, such as by conforming in whole in part on a bone facing side to the shape of the bone as observed or measured using imaging or other devices prior to surgery.

Figure 10:
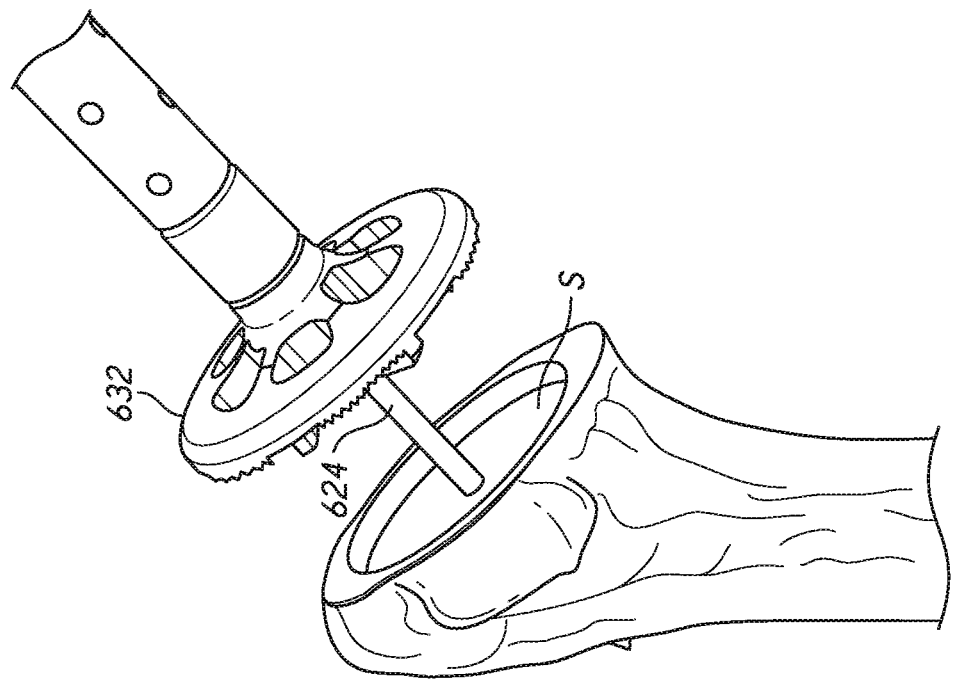

FIG. 10 shows that the resected surface of the head h can be prepared, such as by using a planar or a reamer 632. The reamer 632 also can be guided by the guide pin 624. The reamer 632 can be used to form a recessed surface s to which the assembly 100 will be applied after further preparation.

FIG. 11 shows a step of measuring depth of the recessed surface s. The purpose of this step is to provide a secondary confirmation that the assembly 100 will fit into the metaphysis without striking the lateral cortex. While the analysis of FIG. 9 indicates a diameter of base member 104 that could be used, the depth gauge 637 of FIG. 11 provides a depth sizing that confirms a maximum length, e.g., depth, that would fit in the recessed surface S surgeon is instructed to take the smaller of the two sizes determined.

Figure 13:
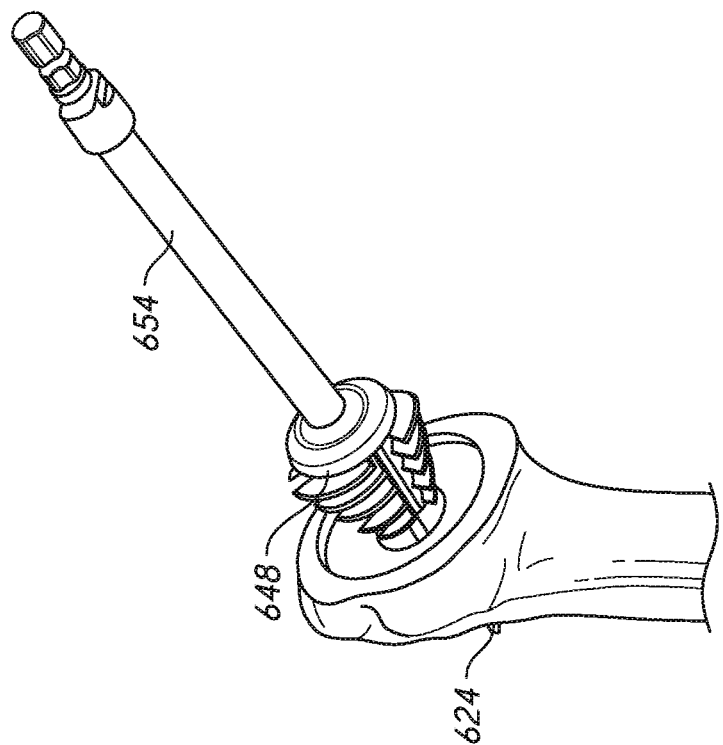

FIG. 12 illustrates that following depth measurement, a bore b is formed in the surface s in initial preparation of the surface s to receive the shoulder assembly 100. The bore b is formed using a drill 640. The drill 640 can be a convention cannulated design configured to be advanced over the guide pin 624. The drill 640 can be configured as a universal drill with a modular stop to obtain variable lengths. The drill 640 can be one of a plurality of drills, each drill of the plurality having a different size as appropriate. In certain methods, the process of forming the bore b and reaming the surface s as discussed above in connection with FIG. 10 can be combined. For example, a drill 640 can have a reaming feature disposed proximally of the bore forming features such that a continuous motion toward the surface formed using the guide 600 can initially form the bore b and subsequently form the surface s. FIG. 13 shows that once the bore b has been formed, the bore b can optionally be tapped to be prepared to receive the base member 104 of the shoulder assembly 100. The tapping process can be achieved by using a helical tap component 648 that is advanced over the guide pin 624. The helical tap 648 can follow the form of the helical structure 224 of the base member 104 such that the base member 104 can be easily advanced into the bore. The helical tap 648 can be secured to a shaft 654 that can be mounted to a motor driven drill or to a hand tool.

Figure 14:
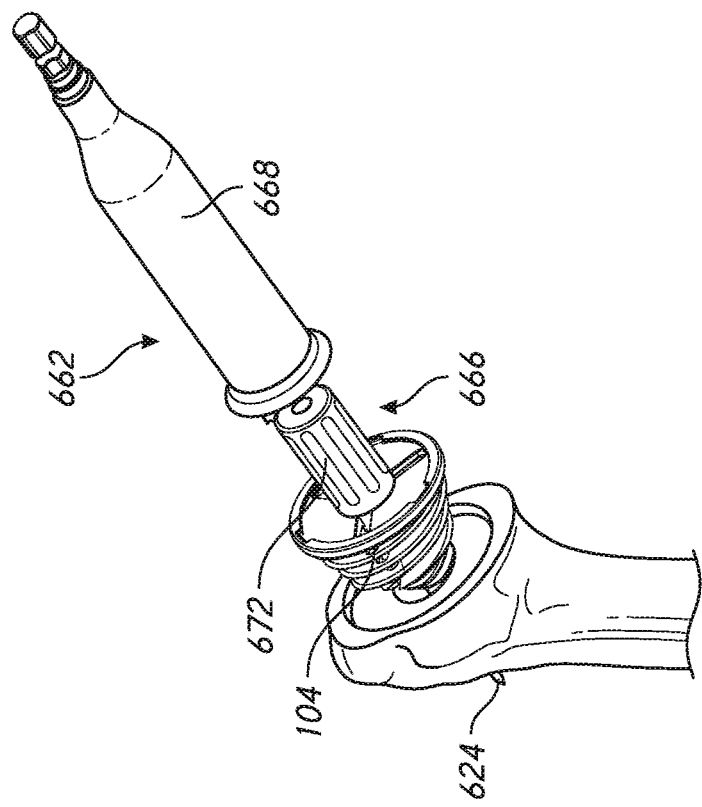

FIG. 14 shows a step of inserting the base member 104. The base member 104 is secured to a distal end of an inerter 662. The inserter 662 has a stem 666 that is threaded at a distal end thereof. The threads of the stem 666 can be mated with the tool interface 272 (see FIG. 7), e.g., with threads of the tool interface. Preferably the stem 666 is enlarged at a mid-section thereof providing at least a shoulder that can mate with the inner raised portion 148 of the base member 104. A separate member 668 of the inserter 662 is advanced over the stem 666 to the tool interface 158, and the force of advancing the base member 104 thus can be applied through the tool interface 272, through the inner raised portion 148, through the apertures 124 or through more than one of these (or other) features of the base member 104. Splines 672 provide for good grip by the surgeon so that the surgeon can easily engage the stem 666 to the tool interface 272. In another variation, a driver with a torqueing device at a proximal end couples at its distal end directly with the tool interface 272, through the inner raised portion 148, through the apertures 124 or through more than one of these (or other) features of the base member 104 to enable more direct transfer of torque to the base member. Preferably inserting the base member 104 into the bone includes placing the outer periphery 154 in the recessed surface s, e.g., at least partially recessed into the resected bone of the humerus H.

Figure 15:
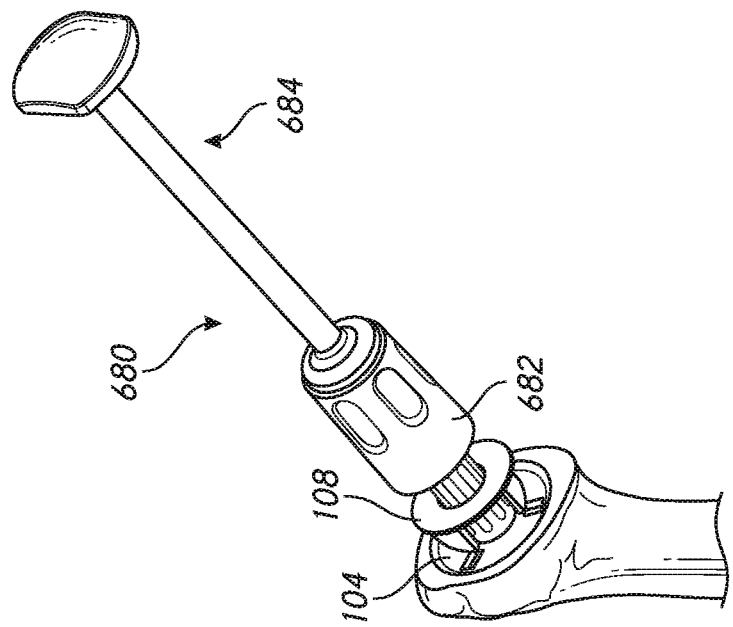
Figure 17:
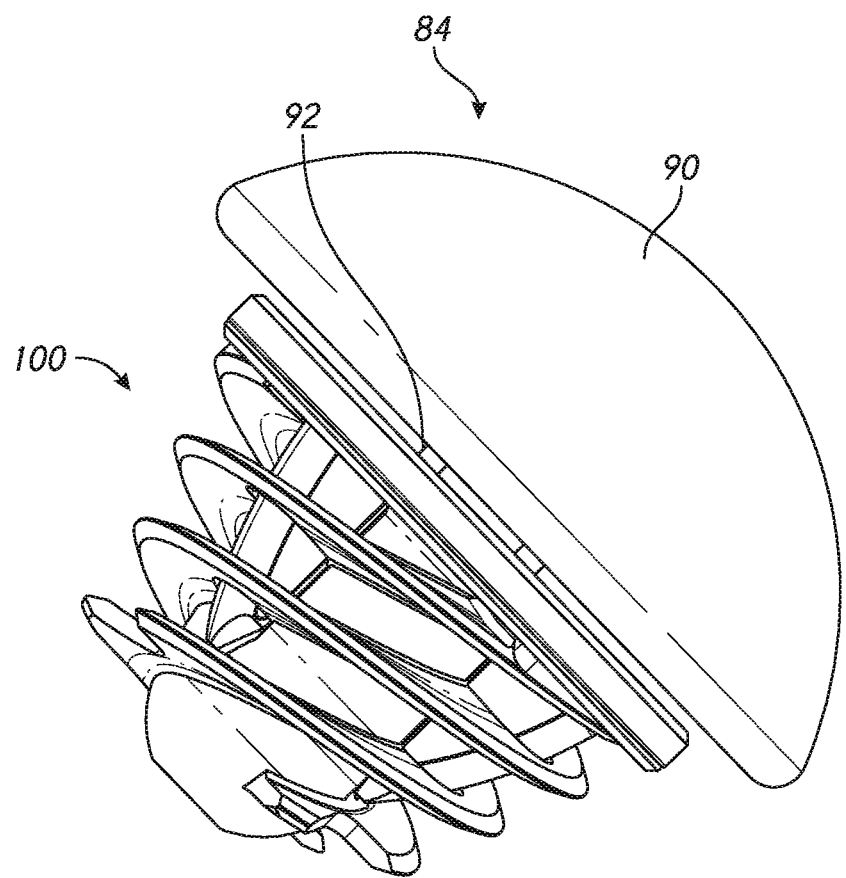
FIG. 17 is a side view of the stemless shoulder assembly of FIG. 2 coupled with an anatomic articular component of the kit illustrated in FIG. 1.

FIG. 15 shows that after the base member 104 has been inserted, the locking device 108 can be inserted. The base member 104 is inserted by a rotation of the member by rotation of the inserter which is directly connected to the base member as discussed above in connection with FIG. 14. The locking device 108 is inserted along the pathway by linear translation, e.g., by a movement along a generally straight axis without rotation. An inserter 680 is provided that has an enlarged head 682 that can be secured to or can just rest upon the proximal face of the annular member 366 of the proximal support 132. The head 682 is then advanced over the splines 672 of the stem 666, with the stem 666 acting as an axial guide. In order to implant the locking device 108 the first end 382 of the arm 110 or arms is aligned with the aperture 124 or apertures if more than one. The arms 110 are radially and circumferentially tapered and the apertures 124 are sized for the wider proximal end of the arms. This configuration helps guide the locking device 108 into the base member 104. The proximal end 684 of the inserter 680 in configured for impacting the locking device 108 into the base member 104.

Figure 16:
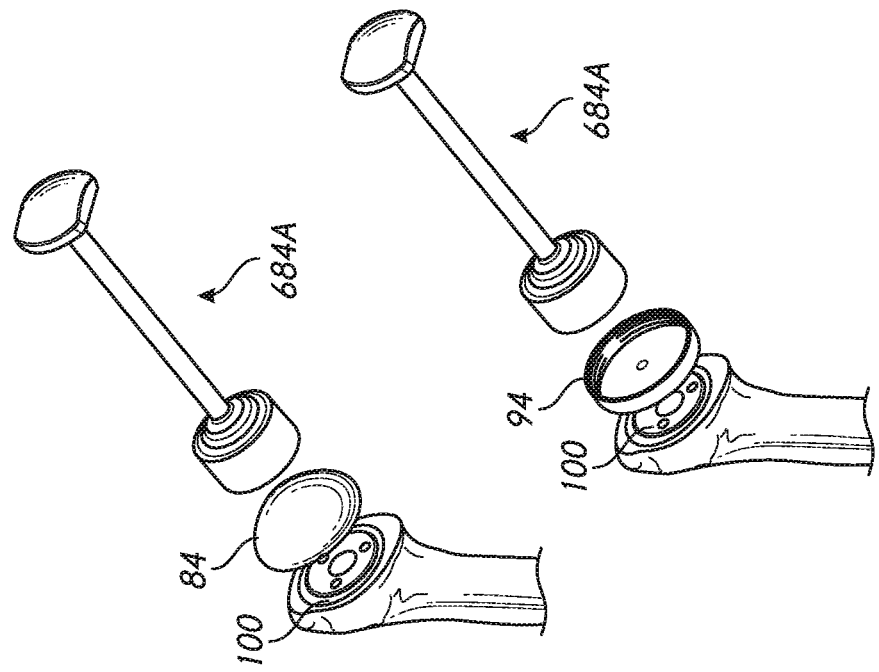
Figure 18A:
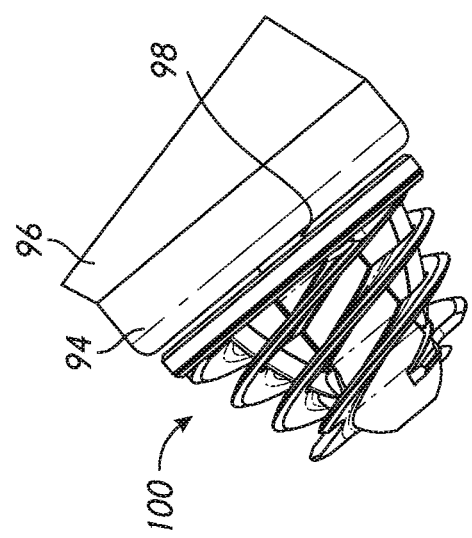
FIG. 18A is a side view of the stemless shoulder assembly of FIG. 2 coupled with a reverse articular component of the kit illustrated in FIG. 1.

FIG. 16 shows later steps of a method of implanting an anatomic shoulder prosthesis. After the base member 104 and the locking device 108 are placed, an anatomic articular component 84 can be coupled with the recess 102. The anatomic articular component 84 comprises a convex surface 90, analogous to the natural anatomy. The anatomic articular component 84 is placed with an impactor 684A. Although shown as a separate, dedicated device the insertion and impaction functions illustrated in FIGS. 15 and 16 could be carried out by the same device. For example a contoured face to contact the surface 84 could have a portion configured for inserting the locking device 108 and/or the tray 94. FIG. 16 shows an alternative step of a method of implanting a reverse shoulder prosthesis. After the base member 104 and the locking device 108 are placed, a reverse articular component 88 can be coupled with the recess 102. In one form, the reverse articular component 88 includes a tray 94. The tray 94 can be coupled with an articular component 96 comprising a concave surface for articulating with a glenoid sphere disposed on a glenoid of a scapula (discussed further below). The tray 94 is placed with an impactor 684A. The reverse shoulder prosthesis including the shoulder assembly 100, the tray 94 and the articular component 96 is shown in FIGS. 18A and 18B. A glenoid sphere 99 mated with a glenoid is shown in FIG. 18B. The shoulder joint provides movement of the patient's arm by articulating the component 96 over the glenoid sphere 99.

In one variation of these methods, assemblies, and kits the locking device 108 is inserted at the same time as some or all of the reverse articular component 88 or at the same time as the anatomic articular component 84. The locking device 108 can be a separate component that is loaded onto an inserter or impacting tool that can be previously loaded with the reverse articular component 88 or the anatomic articular component 84. The locking device 108 can be a separate component that is loaded onto an inserter or impactor with, but relatively moveable to, the reverse articular component 88 or the anatomic articular component 84. The locking device 108 and the reverse articular component 88 can be formed as a monolithic structure that can be loaded together onto an inerter. The locking device 108 and the anatomic articular component 84 can be formed as a monolithic structure that can be loaded together onto an inerter.

III. Additional Apparatuses and Methods

FIGS. 19-23 illustrate a shoulder assembly 800 that is adapted for securement to a glenoid. The shoulder assembly 800 is similar to the shoulder assembly 100 described above, except as described differently below. Any feature discussed above can be substituted in and supplement the features of the shoulder assembly 800. The features of the shoulder assembly 800 can be substituted in and supplement the features of the shoulder assembly 100.

Figure 19:
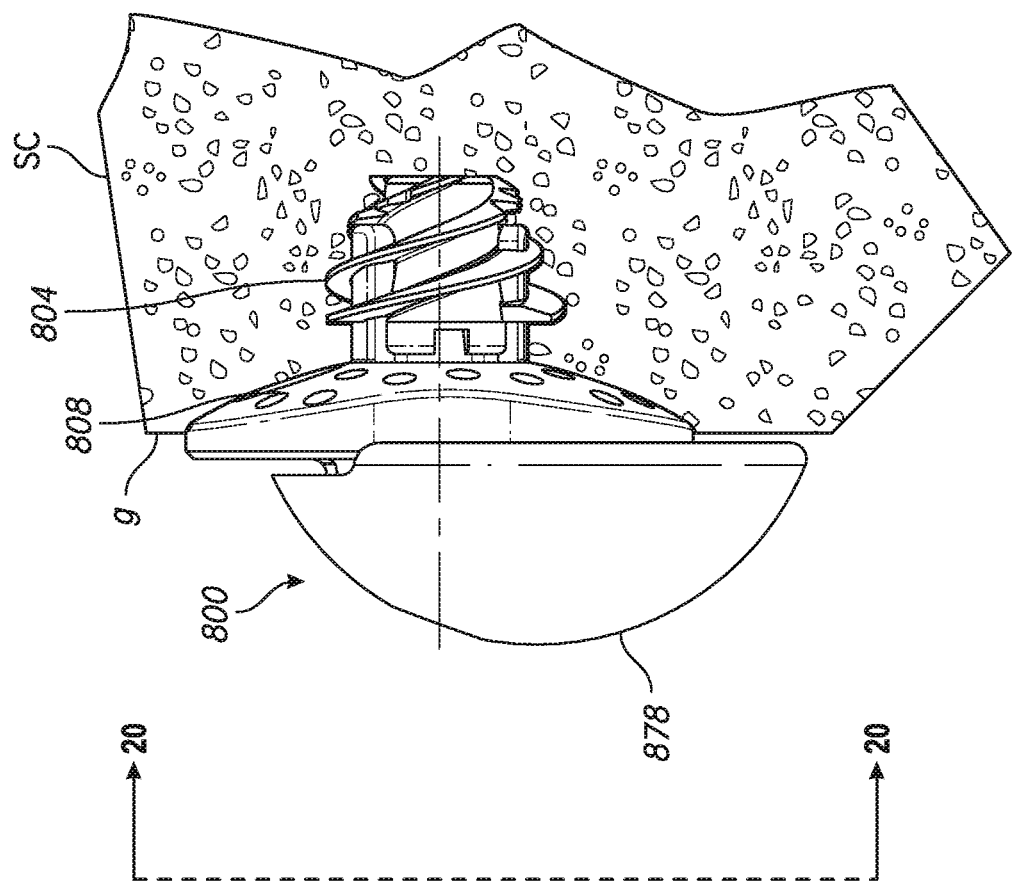
FIG. 19 is a schematic side view of a glenoid of a scapula of a shoulder of a patient with a reverse shoulder prosthesis assembly disposed therein.
Figure 21:
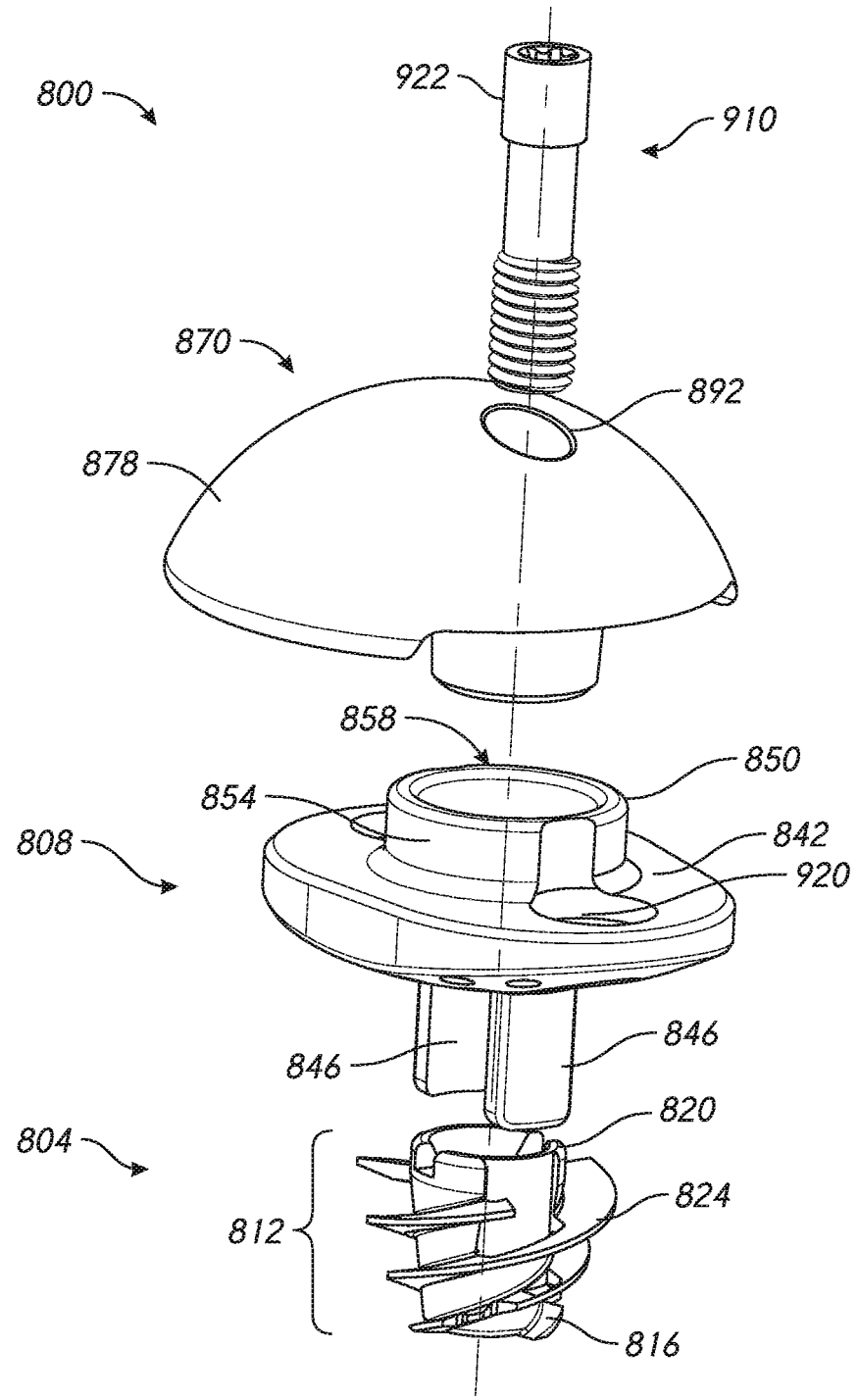
FIG. 21 is an exploded perspective view of the reverse shoulder prosthesis assembly illustrated in FIG. 20 showing features of the articular surface of a glenoid sphere.
Figure 22:
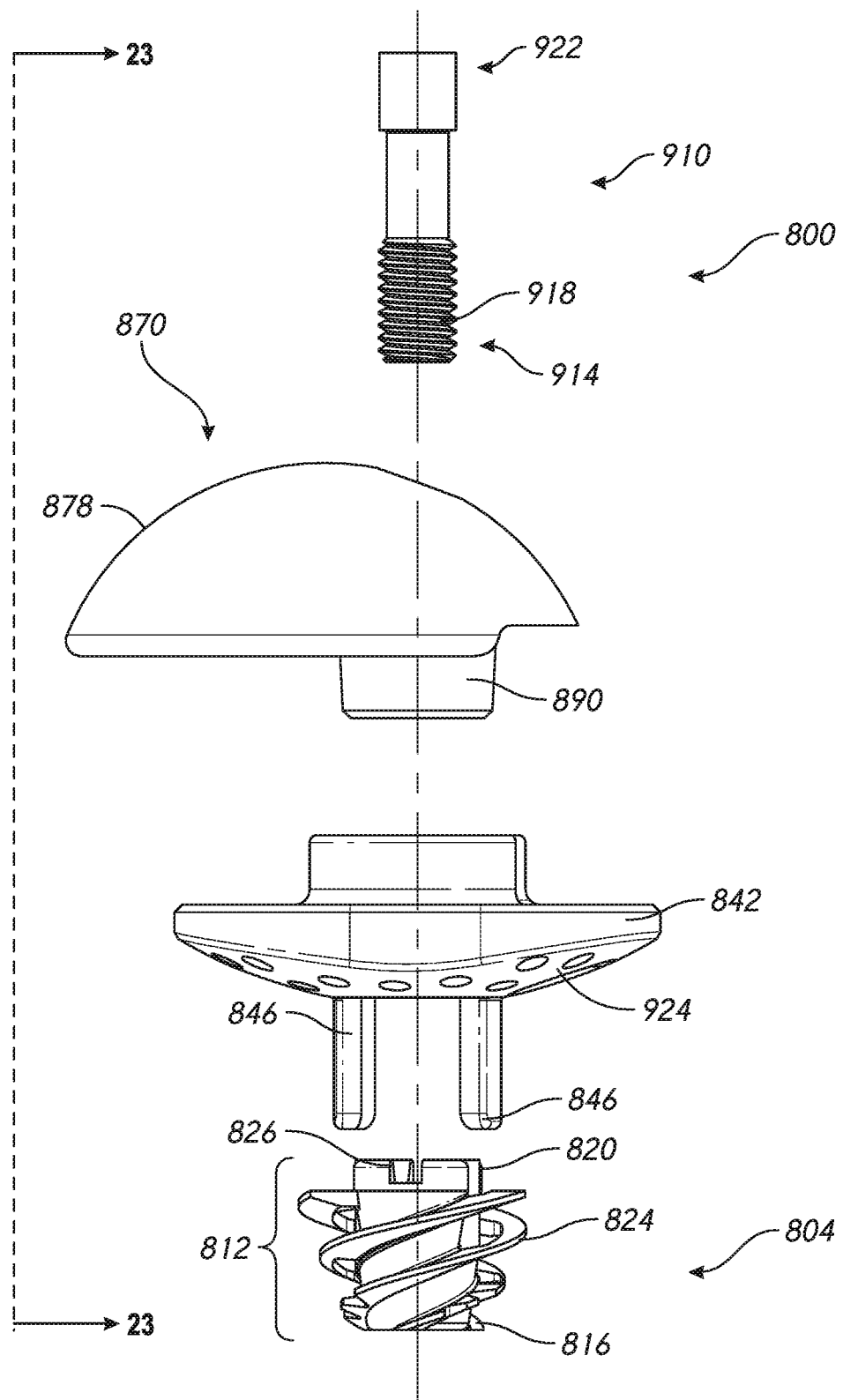
FIG. 22 is an exploded view of the reverse shoulder prosthesis assembly illustrated in FIG. 20 showing features of a bone engaging side of a plate member.
Figure 23:
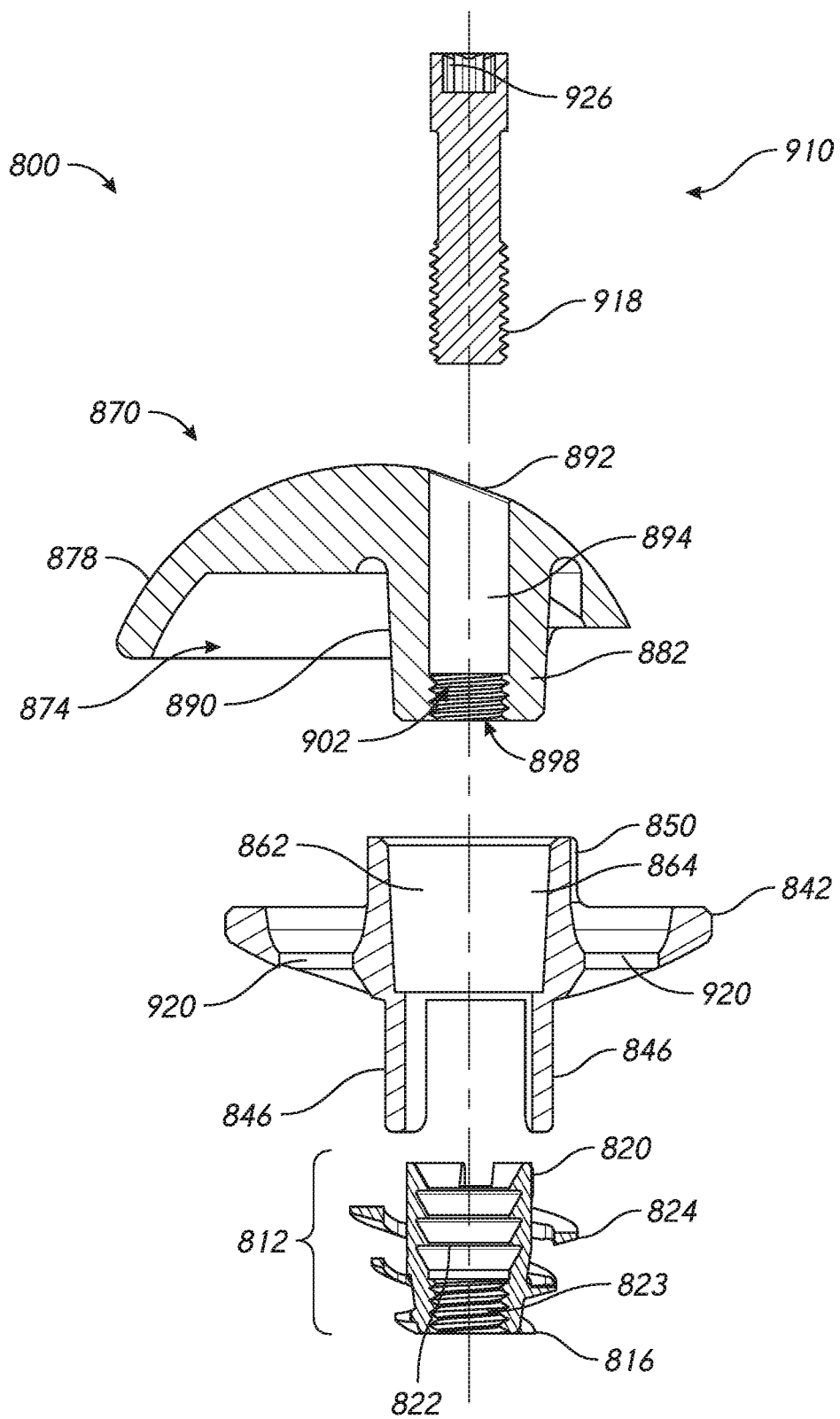
FIG. 23 is a cross-sectional view of the reverse shoulder prosthesis assembly of FIG. 20 taken at section plane 23-23 shown in FIG. 22.

FIG. 19 shows that the shoulder assembly 800 can be implanted into a glenoid region g of a scapula SC. The shoulder assembly 800 includes a base member 804 and a plate member 808. The base member 804 has a medial end 816 and a lateral end 820. FIGS. 21-23 show that the base member 804 includes a body 812 that extends between the medial end 816 and the lateral end 820. A lumen 822 extends in the body 812 from the lateral end 820 toward and in some cases entirely to the medial end 816. A distal portion of the lumen 822 includes a threaded zone 823, discussed below. The base member 804 includes a helical structure 824, which is disposed along the body 812 between the medial and lateral ends 816, 820, respectively. The helical structure 824 extends from the medial end 816 to the lateral end 820 in some embodiments. In some embodiments a tool interface 826 is disposed lateral of a lateral end of the helical structure 824.

Figure 23A:
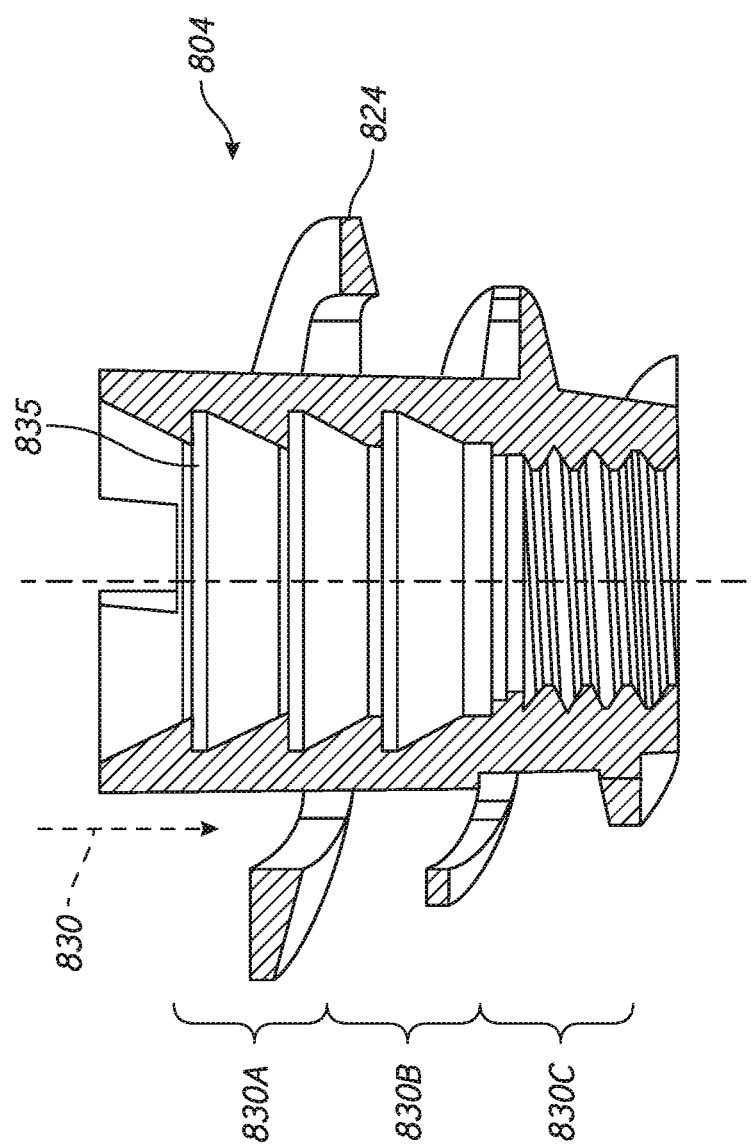
FIG. 23A shows aspects of a base member of the shoulder assembly of FIG. 19.

The base member 804 includes a first pathway 830 accessible from the lateral end 820 of the base member 804. The first pathway 830 is directed toward the medial end 816 through the helical structure 824. The first pathway 830 can be located adjacent to an inner periphery of the helical structure 824, as discussed above. The first pathway 830 can be partly defined by an outer surface of the body 812. The first pathway 830 can be disposed generally transverse to the helical structure 824. The first pathway 830 extends in a space 832 between successive portions of the helical structure 824. In one embodiment, a first segment 830A of the first pathway 830 is disposed through a proximal portion of the helical structure 824, a second segment 830B of the first path 830 is located medial of the first segment 830A, and a third segment 830C of the first path 830 is disposed medial of the second segment 830B. FIG. 23A shows the segments 830A, 830B, 830C of the path 830 in more detail.

FIG. 23A also shows that the base member 804 can include one or more barbs 835. The barbs 835 are configured to facilitate softer material attachment. In some embodiment the internal portion of the base member 804 couples with a structure made of a soft material, such as polyethylene. One example of such an assembly is an anatomic configuration where a convex articular surface may be coupled with the scapula using the base member 804. Another example is a reverse configuration with an inverse bearing surface (e.g. polyethylene glenoid sphere). The mode of connection between the base 804 and an articular or other component can include an interference fit between the barbs 835 and a projection of such component received in a space around which the barbs 835 are located, as described in connection with FIGS. 8A and 8B of WO2016/094739. In other embodiments the barbs 835 can be replaced with mating threads, mating threads and fins and/or mating fins, as described in connection with FIG. 2 of US20120221111. In other embodiments, the barbs 835 can be replaced by a groove and a C-ring or other deflectable member that spans between the base member 804 and an articular or other component as described in connection with FIGS. 4 and 5 of WO2014/067951. The entireties of each of WO2016/094739, US20120221111, and WO2014/067961, including the specific portions of each reference noted above are incorporated by reference herein.

The plate member 808 has a flange 842 and a first arm 846 that projects distally, medially away from or generally in a direction of implantation of the plate member 808 from the flange 842. The plate member 808 can have a second arm 846 that projects away from the flange 842. The first arm 846 is configured to be disposed in the first pathway 830 when the plate member 808 is disposed adjacent to the lateral end 820 of the base member 804. The first arm 846 is disposed through bone in the space 832 between successive portions of the helical structure 824 when the shoulder assembly 800 is implanted.

The plate member 808 also includes a boss 850 that extends laterally of the flange 842. The boss 850 comprises an arcuate outer periphery 854 and an aperture 858 that provides access to a lumen 862 through the aperture 858. The lumen 862 is defined by a tapered surface 864 that mates with a glenoid sphere 870, as discussed below. In another embodiment, the glenoid sphere 870 and the boss 850 are configured such that the glenoid sphere 870 coupled with the outer surface of the boss 850.

The glenoid sphere 870 comprises a recess 874 disposed on a medial side and a convex side 878 disposed opposite the recess 874. The glenoid sphere 870 has a tapered surface 882 disposed within the recess 874. The tapered surface 882 is partly disposed in the recess 874 and partly extends medially of the recess 874. The tapered surface 882 is disposed on a projection 890. The boss 850 receives the projection of the glenoid sphere 870 therein. The tapered surface 864 on the boss 850 mates with the tapered surface 882 on the medial side of the glenoid sphere 870 to form a connection between the glenoid sphere 870 and the plate member 808. The mating tapered surfaces 864, 882 can form a Morse taper connection between the glenoid sphere 870 and the plate member 808.

FIG. 23 illustrates further features of the shoulder assembly 800 that relate to connecting the components thereof together. The glenoid sphere 870 has a lateral opening 892 at the convex surface 878. The opening 892 extends to a lumen 894 that extends from the opening 892 to a medial opening 898. The lumen 894 includes a threaded zone 902 adjacent to the medial opening 898. The threaded zone 902 can be used to couple the glenoid sphere 870 with an inserter. That is the threaded zone 902 can be threaded onto a corresponding threaded tip of the inserter. While threads are shown, other couplers can be used, such as a bayonet coupling in place of or along with the threaded zone 902.

A fastener 910 is used to secure the glenoid sphere 870, the plate member 808, and the base member 804 together. The fastener 910 includes a medial end 914 with a threaded zone 918 and a lateral end 922. The lateral end 922 includes a tool interface 926.

Figure 20:
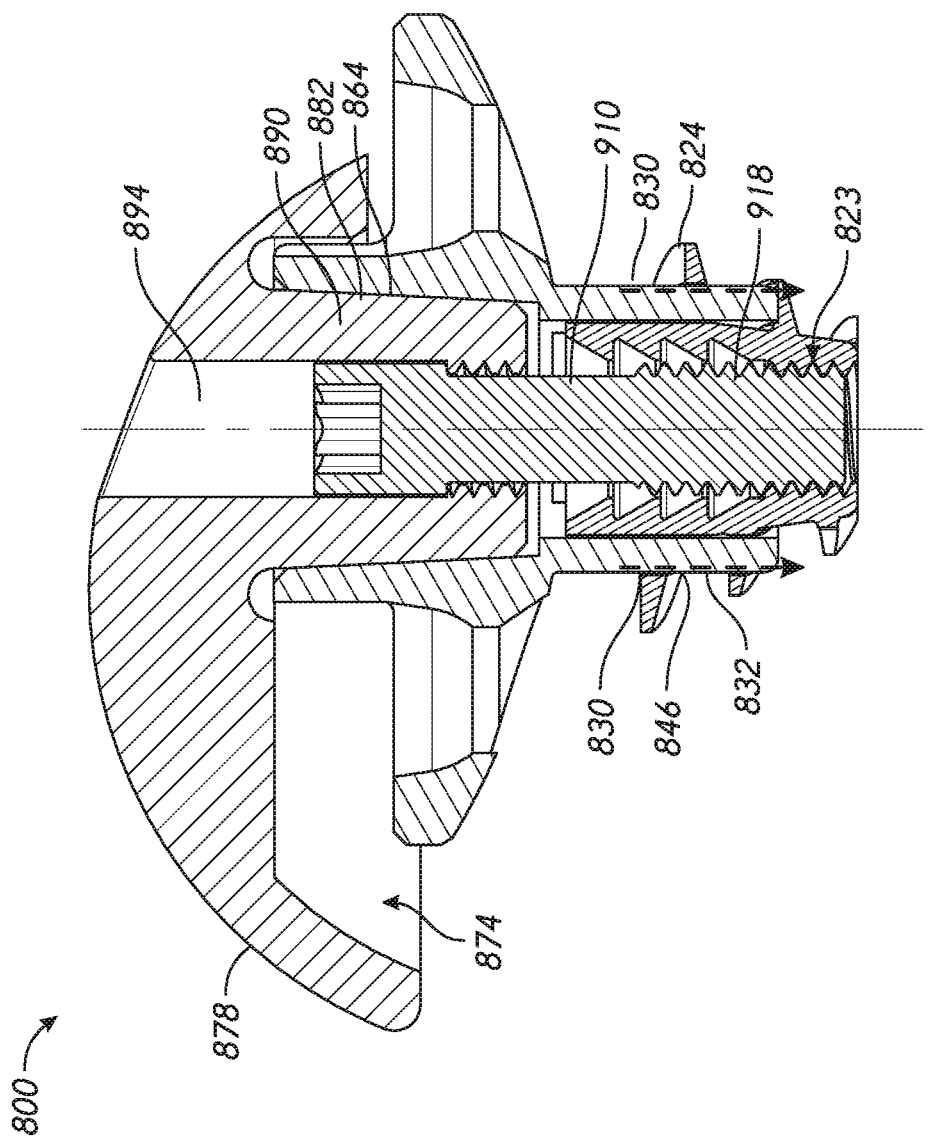
FIG. 20 is a cross-sectional view of the reverse shoulder prosthesis assembly shown in FIG. 19 taken at section plane 20-20.

The connection between the components of the shoulder assembly 900 is shown in FIG. 20. The base member 804 can be advanced into the glenoid g following preparations similar to that discussed in connection with of FIGS. 8-13. Once so placed, the plate member 808 can be advanced into the base member 804. The plate member 808 is advanced in a manner similar to the locking device 108. The arms 846 are advanced into the helical structure 824. Following placement of the plate member 808 into the base member 804, the glenoid sphere 870 can be mated to the plate member. The projection 890 can be advanced into the lumen 862 (see FIG. 23). Once the projection 890 is placed in the lumen 862 the fastener 910 can be advanced relative to the projection 890 and mated with the threaded zone 823. Further advancing of the fastener 910 into the threaded zone 823 induces a friction fit, e.g., a Morse taper, at the tapered surfaces 864, 882. In one embodiment, the threaded zone 918 of the fastener 910 engages first the threaded zone 902 of the glenoid sphere 870 and then mates with the threaded zone 823. In that embodiment, if the threaded zone 918 inadvertently disengage from the threaded zone 823 the back-out of the fastener 910 is limited such that the lateral end 922 of the fastener 910 does not protrude outside of the convex side 878 of the glenoid sphere 870. For example, even if the threaded zone 918 is disengaged form the threaded zone 834, lateral motion of the fastener 910 will be limited when a lateral end of the threaded zone 918 is disposed against a medial end of the threaded zone 902. When in this position, in one embodiment the distance between the lateral end of the threaded zone 918 and the lateral end 922 of the fastener 910 will be less than the distance within the lumen 894 from the lateral end of the threaded zone 902 to the convex side 878 of the glenoid sphere 870. Thus, the disengaged state of the fastener 910 will not result in the lateral end 922 protruding from the convex side 878.

The plate member 808 includes additional features for enhancing securement to the bone. The plate member 808 can includes one or more apertures 920. The apertures 920 can receive bone screws to enhance securement of the plate member 808 to the bone, e.g., to the scapula SC. Advantageously, the bone screw will lock into the apertures 920 by a thread engagement. In some embodiments, the locking mechanism will be multi-directional providing the possibility to lock the bone screws at a variable angle from the axis of the flange 842. Additionally, the medial side of the plate member 808 can includes a textured surface 924 e.g., coated or layered with a porous material in order to accelerate tissue ingrowth such as bony ingrowth. Advantageously, the plate member 808 could be manufactured by additive manufacturing to incorporate the porous surface 924.

Though shown in use to secure a hard material (e.g. ceramic, pyrocarbon, or metal) glenoid sphere 99 to a glenoid, the assembly 800 could be used to secure a soft-material (e.g. polyethylene, polyurethane, PEEK) glenoid sphere. Though shown in use to secure a glenoid sphere 99 to a glenoid, the assembly 800 could be used to secure an atomic glenoid. Though shown in use to secure a glenoid sphere 99 to a glenoid, the assembly 800 could be used in other anatomy to achieve very secure connection to relatively shallow layers of bone, which can include cancellous bone that is exposed during a procedure.

IV. Additional Applications

Figure 24:
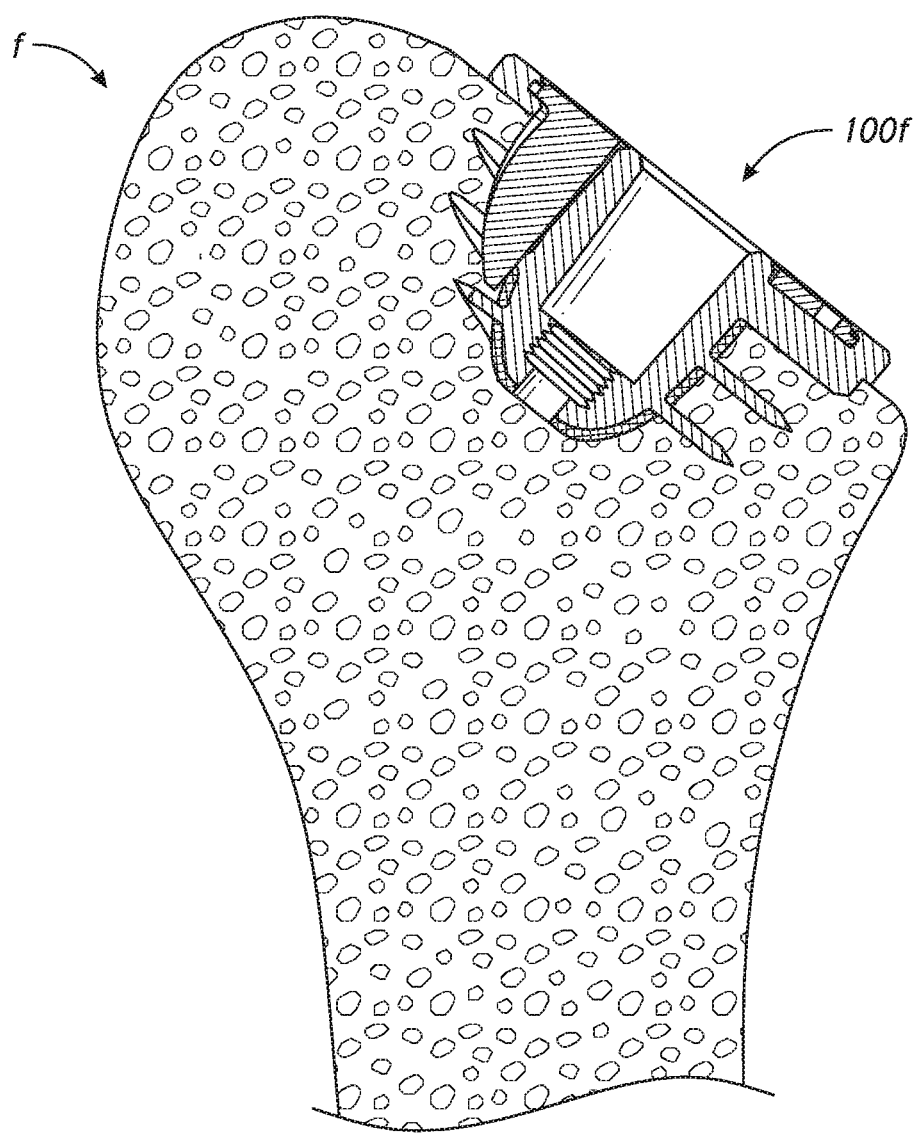
FIG. 24 is a schematic side view of a proximal femur having a prosthesis assembly similar to that of FIGS. 1-7 disposed therein in connection with a hip joint procedure.
Figure 25:
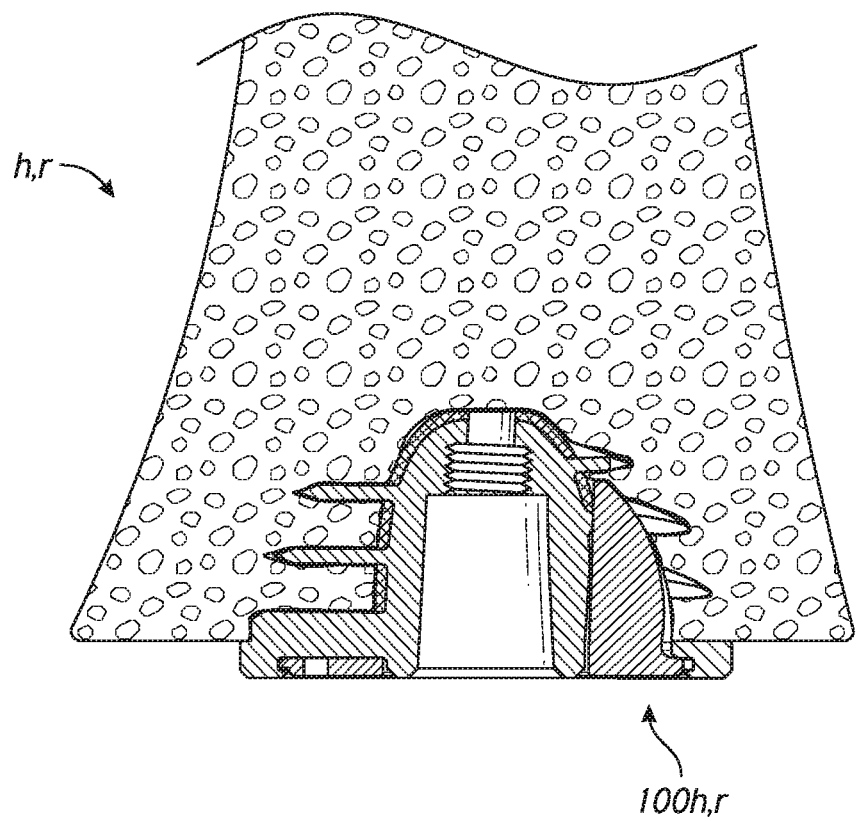
FIG. 25 is a schematic side view of a distal portion of a long bone of an arm, e.g., of the humerus or radius, having a prosthesis assembly similar to that of FIGS. 1-7 disposed therein in connection with an elbow or wrist joint procedure.
Figure 26:
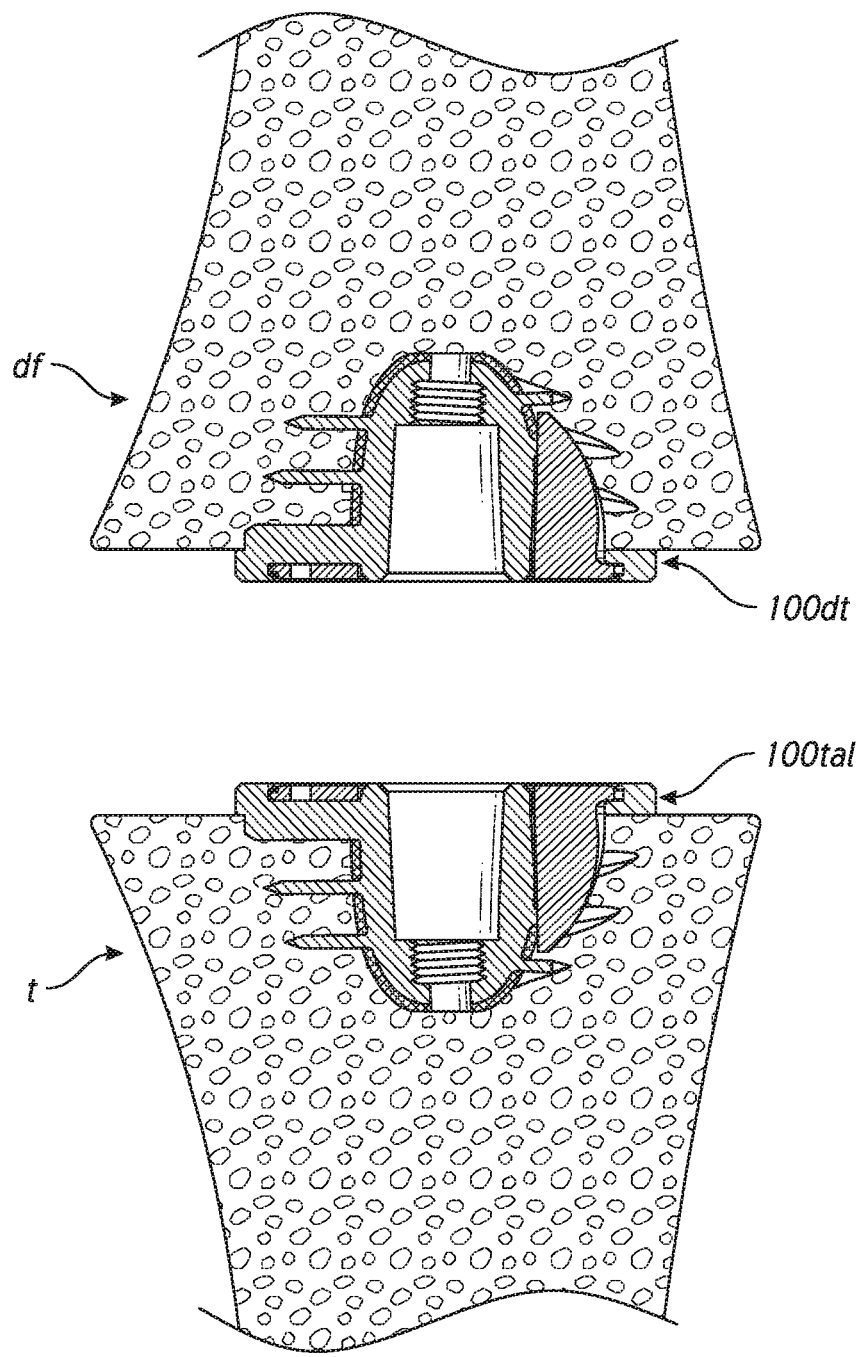
FIG. 26 is a schematic side view of a knee joint showing a prosthesis assembly similar to that of FIGS. 1-7 disposed in the distal femur and in the proximal tibia thereof.
Figure 27:
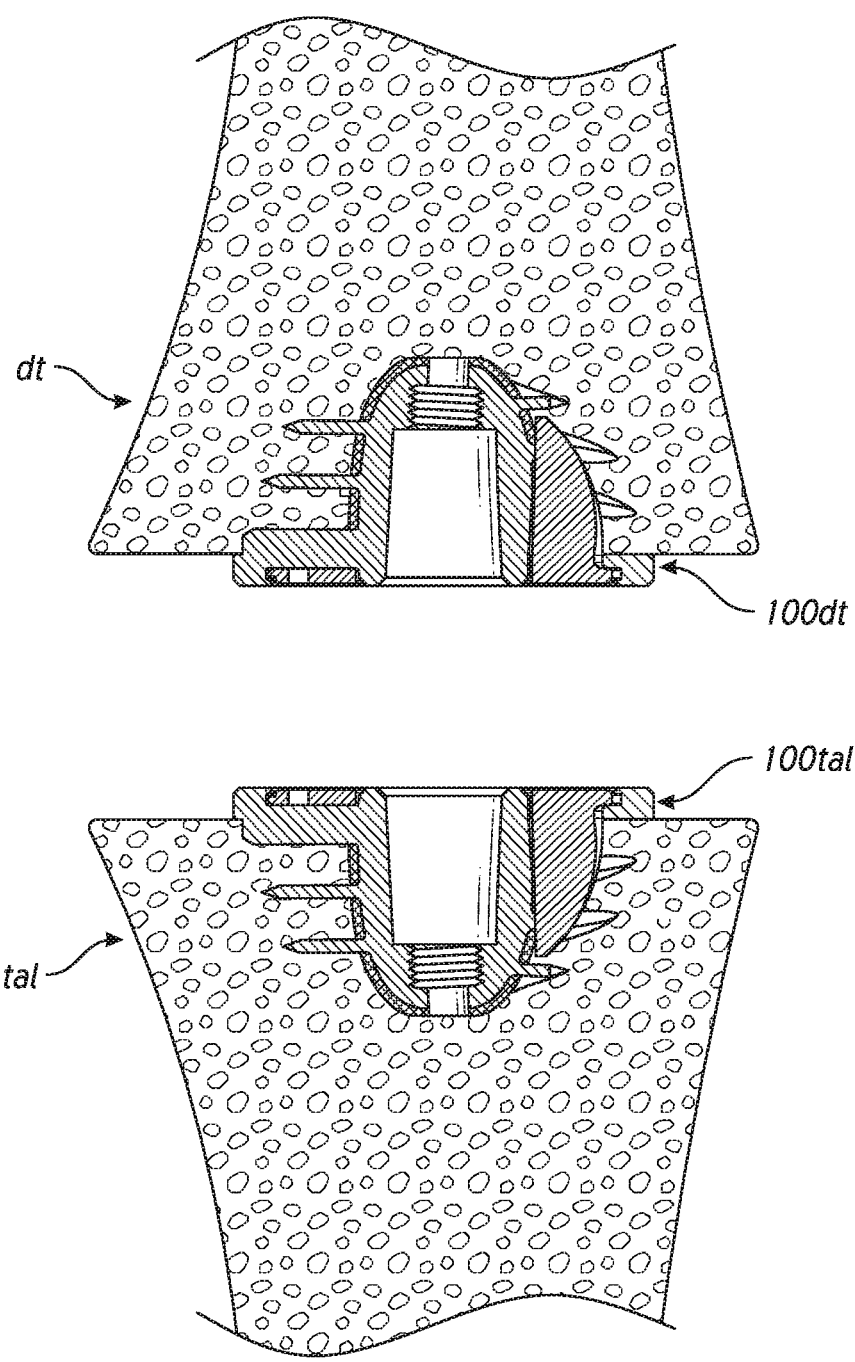
FIG. 27 is a schematic side view of an ankle joint showing a prosthesis assembly similar to that of FIGS. 1-7 disposed in the distal tibia and in the proximal talus thereof.

FIGS. 24-26 show a number of other applications for the prosthesis assemblies described herein. In particular, the shoulder assemblies 100, 800 can be applied to other bones and joints.

FIG. 24 shows that a proximal femur f can be fitted with a prosthesis assembly 100f similar to the prosthesis assembly 100. The prosthesis assembly 100f is different from the shoulder assembly 100 in that it would be configured more particularly for the proximal femur.

FIG. 25 shows that a distal humerus h or to a distal radius r can be fitted with a prosthesis assembly 100*h, r* similar to the prosthesis assembly 100. The prosthesis assembly 100*h, r* is different from the shoulder assembly 100 in that it would be configured more particularly for the distal humerus or radius.

FIG. 26 shows that a distal femur df and/or to a proximal tibia t can be fitted with a prosthesis assembly 100*df*, 100*t* similar to the prosthesis assembly 100. The prosthesis assemblies 100*df, t*, are different from the shoulder assembly 100 in that they would be configured more particularly for the distal femur or proximal tibia. Also, on both side of the knee joint, implant sizing such as threads external diameter, core diameter, overall length could be sized according to patient anatomy per pre-operative planning based on CT-scan, MRI or any other medical images modality.

FIG. 27 shows that a distal tibia dt and/or to a proximal talus tal can be fitted with a prosthesis assembly 100*dt*, 100*tal* similar to the prosthesis assembly 100. The prosthesis assemblies 100*dt, tal*, are different from the shoulder assembly 100 in that they would be configured more particularly for the distal tibia or proximal talus. Also, on both side of the ankle joint, implant sizing such as threads external diameter, core diameter, overall length could be sized according to patient anatomy per pre-operative planning based on CT-scan, MRI or any other medical images modality.

Each of the applications illustrated in FIGS. 24-26 can employ the prosthesis assembly 800 with modifications similar to those discussed above in connection with the prosthesis assemblies 100*h*, 100*r*, 100*f*, and 100*t*.

V. Performance of Embodiments Disclosed Herein

Figure 28:
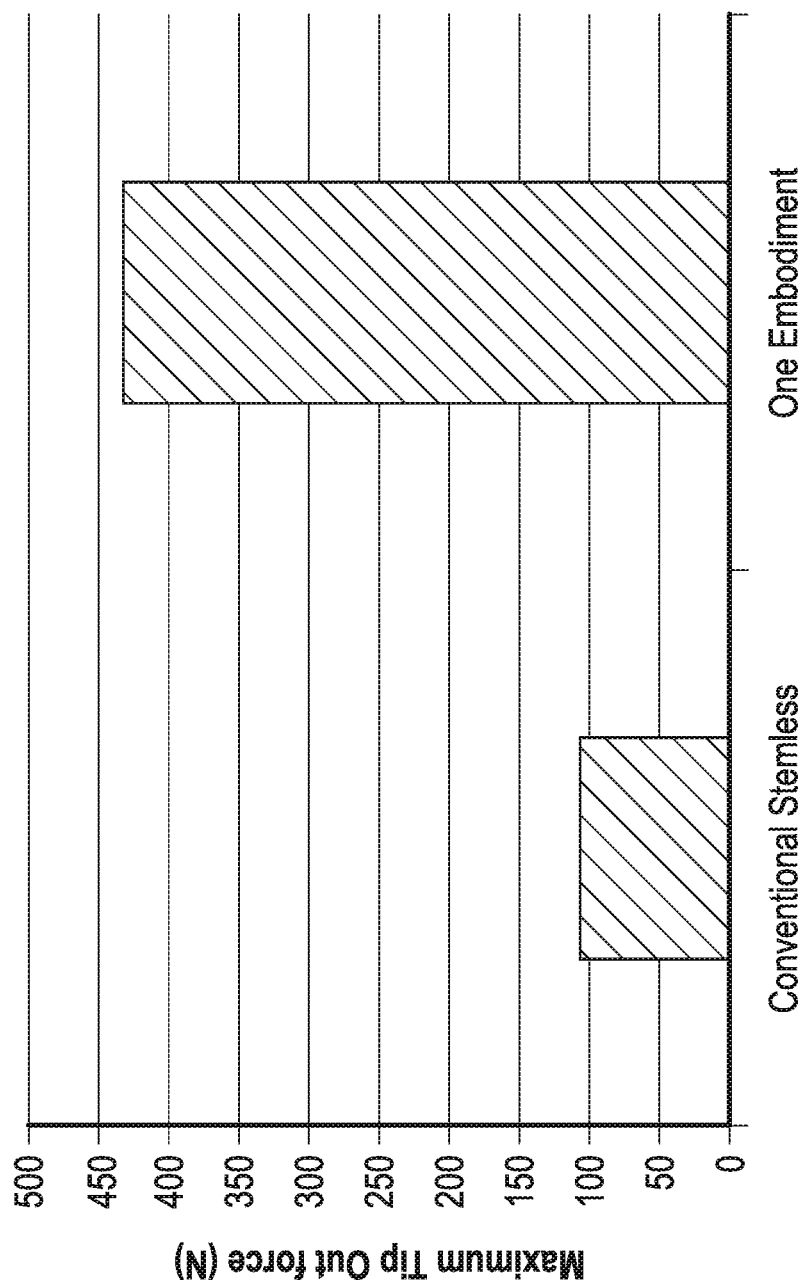
FIG. 28 shows comparative tip out performance of an embodiment as disclosed herein compared to a conventional stemless implant.

FIG. 28 shows comparative performance of embodiments disclosed herein with respect to a stemless apparatus that does not have the helical structures disclosed herein nor the locking devices. The graph shows maximum tip out force which is measured by applying an off axis load at a known or prescribed fixed distance from a surface at or to which a shoulder assembly similar to the assembly 100 was implanted. The tip out force represents the resistance of the device to tipping out or becoming dislodge from the surface when subject to off axis loading. The forces were observed using a load cell or force transducer. As can be seen, the force of one embodiment is more than four times the force that would dislodge the conventional stemless component. This represents a significant improvement in the retention of the apparatuses disclosed herein compared to conventional stemless design which rely to a large extent on ingrowth for securement which can be sufficient some time after implantation but which can be subject to dislodgement prior to full integration by ingrowth.

As used herein, the relative terms "proximal" and "distal" shall be defined from the perspective of the humeral shoulder assembly. Thus, distal refers the direction of the end of the humeral shoulder assembly embedded in the humerus, while proximal refers to the direction of the end of the humeral shoulder assembly facing the glenoid cavity when the assembly is applied to the humerus. Distal refers the direction of the end of the humeral shoulder assembly embedded in the scapula, while proximal refers to the direction of the end of the humeral shoulder assembly facing the humerus when the assembly is applied to the glenoid. In the context of a glenoid component, the distal end is also sometimes referred to as a medial end and the proximal end is sometimes referred to as a lateral end.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A shoulder prosthesis comprising:
   a base that is one piece and includes:
      a collar including:
         a plurality of apertures circumferentially spaced apart around the collar; and
         a plurality of notches circumferentially spaced apart around the collar;
      a body extending distally from the collar;
      a helical structure extending directly from and around the body; and
      an inner portion including a recess projecting distally from the collar to a distal end of the shoulder prosthesis, the recess extending through the body, wherein
   the plurality of apertures are shaped such that a length extending radially between the inner portion and an outer periphery of the collar is longer than a width extending perpendicular to the length; and
   the plurality of notches extend farther radially outward relative to the plurality of apertures.

2. The shoulder prosthesis of claim 1, wherein each of the plurality of notches is positioned circumferentially between two adjacent apertures of the plurality of apertures.

3. The shoulder prosthesis of claim 1, wherein the collar comprises a recessed region positioned radially between the recess and the outer periphery of the collar.

4. The shoulder prosthesis of claim 1, wherein the body comprises a cylindrical portion.

5. The shoulder prosthesis of claim 1, wherein a portion of the body extends distally of the helical structure.

6. The shoulder prosthesis of claim 1, wherein the shoulder prosthesis is stemless.

7. The shoulder prosthesis of claim 1, further comprising:
   a first pathway projecting distally of the collar and through the helical structure adjacent to an inner periphery thereof, the first pathway being generally transverse to the helical structure and extending in a space between successive portions of the helical structure.

8. A shoulder assembly comprising:
   the shoulder prosthesis of claim 7; and
   a locking device comprising a proximal support and a first arm projecting distally of the proximal support, the first arm configured to be disposed in the first pathway projecting distally of the collar when the proximal support is disposed adjacent to the collar;
   wherein the first arm is configured to be disposed through bone in the space between successive portions of the helical structure when the shoulder assembly is implanted.

9. The shoulder assembly of claim 8, further comprising an outer periphery of the helical structure surrounding the recess, the first arm being located between the outer periphery of the helical structure and the recess.

10. The shoulder assembly of claim 8, wherein the first arm comprises an inner edge and an outer edge positioned radially outward of the inner edge, at least the outer edge of the first arm disposed in the helical structure along the first pathway.

11. The shoulder assembly of claim 8, wherein the proximal support comprises an annular member.

12. The shoulder assembly of claim 8, further comprising a second arm, the second arm being circumferentially spaced apart from the first arm.

13. The shoulder assembly of claim 8, wherein the proximal support comprises an engagement feature to engage the collar.

14. The shoulder assembly of claim 8, wherein at least one of the first arm and the first pathway comprise an engagement feature to engage the other of the first arm and the first pathway.

15. The shoulder assembly of claim 8, wherein first arm is configured to be disposed through bone between the collar and the helical structure.

16. A kit comprising:
   the shoulder prosthesis of claim 1;
   an anatomic articular component mateable with the shoulder prosthesis, the anatomic articular component comprising a convex articular surface adapted to articulate with a concave surface of or on a scapula of a patient; and
   a reverse articular component mateable with the shoulder prosthesis, the reverse articular component comprising a concave articular surface adapted to articulate with a convex surface on a scapula of a patient.

* * * * *